(12) United States Patent
Mastrototaro et al.

(10) Patent No.: US 10,561,789 B2
(45) Date of Patent: *Feb. 18, 2020

(54) USER-CONFIGURABLE CLOSED-LOOP NOTIFICATIONS AND INFUSION SYSTEMS INCORPORATING SAME

(71) Applicant: MEDTRONIC MINIMED, INC., Northridge, CA (US)

(72) Inventors: John J. Mastrototaro, Los Angeles, CA (US); Desmond Barry Keenan, Valencia, CA (US); Benyamin Grosman, Valley Village, CA (US); Anirban Roy, Agoura Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/828,339

(22) Filed: Nov. 30, 2017

(65) Prior Publication Data

US 2018/0085523 A1 Mar. 29, 2018

Related U.S. Application Data

(63) Continuation of application No. 14/174,487, filed on Feb. 6, 2014, now Pat. No. 9,861,748.

(51) Int. Cl.
*A61M 5/172* (2006.01)
*A61M 5/142* (2006.01)
*A61M 5/145* (2006.01)

(52) U.S. Cl.
CPC ...... *A61M 5/1723* (2013.01); *A61M 5/14248* (2013.01); *A61M 5/1452* (2013.01); *A61M 2005/14208* (2013.01); *A61M 2205/18* (2013.01); *A61M 2205/3365* (2013.01); *A61M 2205/3569* (2013.01); *A61M 2205/3592* (2013.01); *A61M 2205/70* (2013.01);
(Continued)

(58) Field of Classification Search
CPC ............ A61M 5/1723; A61M 5/14244; A61M 5/172; A61M 5/14248; A61M 5/142; A61M 5/14276; A61M 5/16831; A61M 5/1452; A61B 5/14532; A61B 5/4839; G06F 19/3468; G06F 19/3456; G16H 20/17

See application file for complete search history.

(56) References Cited

U.S. PATENT DOCUMENTS

| 4,562,751 A | 1/1986 | Nason et al. |
| 4,685,903 A | 8/1987 | Cable et al. |

(Continued)

OTHER PUBLICATIONS

Thomann, et al., An Efficient Monitoring Concept With Control Charts for On-Line Sensors, 2002, Water Science and Technology, vol. 46, No. 4-5, pp. 107-116.

*Primary Examiner* — Manuel A Mendez
(74) *Attorney, Agent, or Firm* — Lorenz & Kopf, LLP

(57) ABSTRACT

Infusion systems, infusion devices, and related operating methods are provided. An exemplary method of operating an infusion device capable of delivering fluid to a user involves storing alert configuration information for the user, identifying an alert condition while operating the infusion device to deliver the fluid based at least in part on the alert configuration information for the user, and in response to identifying the alert condition, providing a user notification in accordance with the user's stored alert configuration information.

20 Claims, 10 Drawing Sheets

(52) U.S. Cl.
CPC ............... *A61M 2205/702* (2013.01); *A61M 2205/8212* (2013.01)

(56) References Cited

U.S. PATENT DOCUMENTS

| | | | |
|---|---|---|---|
| 4,755,173 A | 7/1988 | Konopka et al. | |
| 5,080,653 A | 1/1992 | Voss et al. | |
| 5,097,122 A | 3/1992 | Colman et al. | |
| 5,391,250 A | 2/1995 | Cheney, II et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,088,608 A | 7/2000 | Schulman et al. | |
| 6,119,028 A | 9/2000 | Schulman et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,740,072 B2 | 5/2004 | Starkweather et al. | |
| 6,749,587 B2 | 6/2004 | Flaherty | |
| 6,752,787 B1 | 6/2004 | Causey, III et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,827,702 B2 | 12/2004 | Lebel et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,323,142 B2 | 1/2008 | Pendo et al. | |
| 7,399,277 B2 | 7/2008 | Saidara et al. | |
| 7,402,153 B2 | 7/2008 | Steil et al. | |
| 7,442,186 B2 | 10/2008 | Blomquist | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,603,026 B2 | 12/2013 | Favreau | |
| 9,861,748 B2 * | 1/2018 | Mastrototaro ...... A61M 5/1723 | |
| 2007/0123819 A1 | 5/2007 | Mernoe et al. | |
| 2008/0269714 A1 | 10/2008 | Mastrototaro et al. | |
| 2010/0057042 A1 | 3/2010 | Hayter | |
| 2010/0160861 A1 | 6/2010 | Causey, III et al. | |
| 2011/0098674 A1 | 4/2011 | Vicente et al. | |
| 2011/0233393 A1 | 9/2011 | Hanson et al. | |
| 2012/0323100 A1 | 12/2012 | Kamath et al. | |
| 2013/0060112 A1 | 3/2013 | Pryor et al. | |
| 2013/0296677 A1 | 11/2013 | Pryor et al. | |
| 2013/0324824 A1 | 12/2013 | Kamath et al. | |
| 2014/0005505 A1 | 1/2014 | Peyser et al. | |
| 2014/0012117 A1 | 1/2014 | Mensinger et al. | |
| 2014/0012118 A1 | 1/2014 | Mensinger et al. | |
| 2014/0012510 A1 | 1/2014 | Mensinger et al. | |
| 2014/0039383 A1 | 2/2014 | Dobbles et al. | |
| 2014/0052091 A1 | 2/2014 | Dobbles et al. | |
| 2014/0052092 A1 | 2/2014 | Dobbles et al. | |
| 2014/0052093 A1 | 2/2014 | Dobbles et al. | |
| 2014/0052094 A1 | 2/2014 | Dobbles et al. | |
| 2014/0052095 A1 | 2/2014 | Dobbles et al. | |
| 2014/0066889 A1 | 3/2014 | Grosman et al. | |
| 2014/0114154 A1 | 4/2014 | Kamath et al. | |
| 2014/0114278 A1 | 4/2014 | Dobbles et al. | |
| 2014/0128703 A1 | 5/2014 | Simpson et al. | |
| 2014/0128704 A1 | 5/2014 | Simpson et al. | |
| 2014/0128803 A1 | 5/2014 | Dobbles et al. | |
| 2014/0180049 A1 | 6/2014 | Brauker et al. | |
| 2014/0221966 A1 | 8/2014 | Buckingham et al. | |
| 2016/0183856 A1 | 6/2016 | Pryor et al. | |
| 2016/0198988 A1 | 7/2016 | Bhavaraju et al. | |

* cited by examiner

USER-CONFIGURABLE CLOSED-LOOP NOTIFICATIONS AND INFUSION SYSTEMS INCORPORATING SAME

CROSS-REFERENCES TO RELATED APPLICATIONS

This application is a continuation of U.S. patent application Ser. No. 14/174,487, filed Feb. 6, 2014. The subject matter of this application is also related to U.S. patent application Ser. No. 15/828,340, filed concurrently herewith.

TECHNICAL FIELD

Embodiments of the subject matter described herein relate generally to medical devices, and more particularly, embodiments of the subject matter relate to generating user notifications while providing closed-loop control of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. It is desirable to provide continuous insulin infusion control schemes that are capable of safely regulating a user's blood glucose level without interfering with the user's daily activities (e.g., without waking a user overnight). That said, some users prefer a more hands-on approach to managing their blood glucose level.

BRIEF SUMMARY

An embodiment of a method of operating an infusion device capable of delivering fluid to a user is provided. An exemplary method involves storing alert configuration information for the user, identifying an alert condition while operating the infusion device to deliver the fluid based at least in part on the alert configuration information for the user, and in response to identifying the alert condition, providing a user notification in accordance with the stored alert configuration information.

In one embodiment, an infusion system is provided that includes one or more user interface elements, a motor operable to deliver fluid that influences a condition of a user to the user, a sensing arrangement to obtain a sensor value indicative of the condition of the user, a data storage element to store alert configuration information for the user, and a control system coupled to the motor, the sensing arrangement, the data storage element, and the one or more user interface elements. The control system is configured to operate the motor in a closed-loop mode to deliver the fluid to the user based at least in part on a difference between a target value for the condition of the user and the sensor value, identify an alert condition based at least in part on the alert configuration information for the user while operating the motor in the closed-loop mode, and in response to identifying the alert condition, provide a user notification via the one or more user interface elements in accordance with the alert configuration information.

In another embodiment, a method of operating an infusion device capable of delivering insulin to a user involves maintaining user-specific alert configuration information for the user and operating the infusion device in a closed-loop mode to deliver insulin to the user based on a difference between a target glucose value for the user and a sensor glucose value for the user obtained using a glucose sensing arrangement. The closed-loop mode is based at least in part on an initial blood glucose reference measurement value for the user and an initial calibration factor for the glucose sensing arrangement. The method further involves identifying an alert condition while operating the infusion device in the closed-loop mode based at least in part on the user-specific alert configuration information, automatically providing a user notification in accordance with the user-specific alert configuration information in response to identifying the alert condition, and after providing the user notification, receiving an updated blood glucose reference measurement value and operating the infusion device to deliver the insulin to the user in a manner that is influenced by the updated blood glucose reference measurement value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
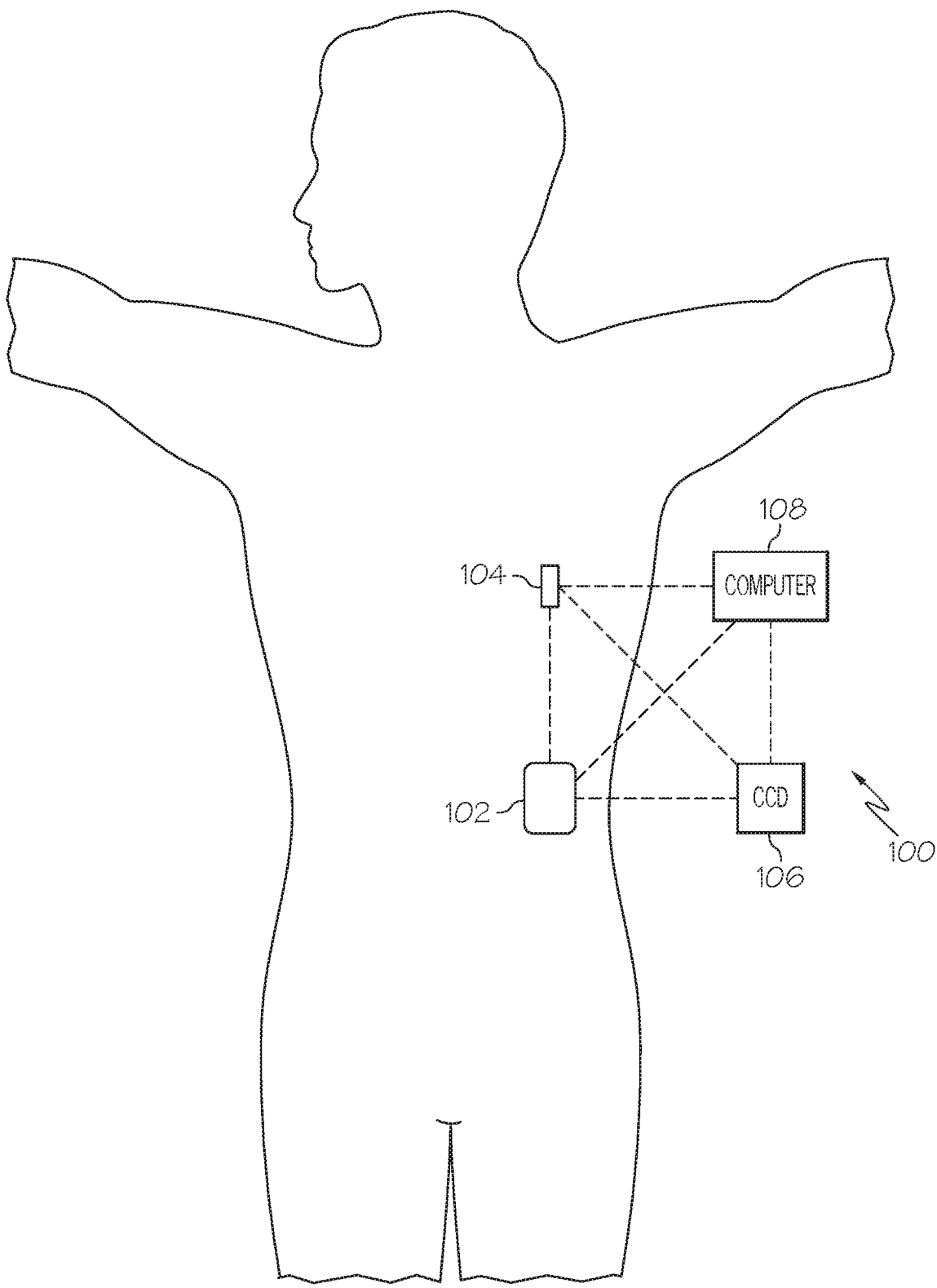
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to displace a plunger (or stopper) of a reservoir provided within the fluid infusion device and deliver a dosage of fluid, such as insulin, to the body of a user. As described in greater detail below, during a closed-loop control mode, delivery commands (or dosage commands) that govern operation of the motor are determined based on a difference between a measured value for a condition in the body of the user and a target value to regulate the condition in the body of the user to the target value. While operating the infusion device to provide closed-loop control, a number of different conditions may be detected that are indicative of potential anomalous conditions that may impact the operations of the closed-loop control. For example, limits or other thresholds imposed to prevent inadvertent overdelivery or underdelivery, ensure sensing arrangements are functioning properly within their calibration range, and the like. These conditions detected while operating the infusion device in the closed-loop mode may be used to initiate or otherwise trigger an alternative control of the infusion device instead of the closed-loop control (e.g., an open-loop mode, or the like). Additionally, the conditions detected while operating the infusion device in the closed-loop mode may be used to initiate or otherwise trigger the generation of user notifications or alerts, and accordingly, such conditions that may be detected during the closed-loop mode are alternatively referred to herein as alert conditions.

In exemplary embodiments, the user notifications that are provided in response to detection of a particular alert condition during the closed-loop mode are configurable for the individual user associated with the infusion device. In other words, each user may define an alerting scheme that is unique and tailored to his or her individual preferences, and thus, the user notifications are generated in a user-specific manner based on that user's alert configuration information. In this regard, whether or not a user notification is generated for a particular alert condition may be chosen by the user, and furthermore, the type and/or number of user notifications generated for a particular alert condition may also be chosen by the user. Additionally, the user may configure other parameters associated with the user notifications, such as, for example, whether a user notification should be repeated and/or how frequently a user notification should be repeated if the user has not responded to the notification, what user-specific thresholds should be utilized to determine the type and/or number of user notifications to be generated, the content of the user notifications, one or more destination addresses for a user notification (e.g., for a remote notification via text message, e-mail, or the like), and the like.

As described in greater detail below in the context of FIGS. 9-10, the alert configuration information for an individual user is received and stored or otherwise maintained for reference during the closed-loop mode. During the closed-loop mode, when an alert condition is identified, the user's alert configuration information is consulted to determine whether any user notifications should be generated, and if so, the type and/or number of user notifications to be generated. Thereafter, the appropriate user notifications are automatically generated in accordance with the user-specific alert configuration information. After a user notification is generated, the user may submit or otherwise provide a response to the user notification, whereby the subsequent operation of the infusion device is influenced by the response to the user notification.

For example, the user may manipulate a blood glucose meter (e.g., a finger stick device or the like) to submit an updated (or new) blood glucose measurement from the body of the user for use as an updated (or new) reference value for the closed-loop control. Based on the updated blood glucose reference measurement value, the functionality and/or operation of the closed-loop control may be verified or otherwise confirmed, for example, by comparing the updated blood glucose reference measurement value to recent sensor glucose measurement values determined based on the measurement data from another glucose sensing arrangement (e.g., an interstitial glucose sensing arrangement). When the accuracy of the closed-loop control and/or the glucose sensing arrangement is verified, the closed-loop mode is reinitialized, restarted, or otherwise reinitiated based at least in part on the updated blood glucose reference measurement value, such that closed-loop operation of the infusion device is provided or otherwise maintained after the alert condition was detected. If the updated blood glucose reference measurement value indicates that the glucose sensing arrangement is out of calibration by an amount that can be corrected by recalibration, one or more updated (or new) sensor calibration factors are determined using the updated blood glucose reference measurement value before reinitializing the closed-loop mode using the updated blood glucose reference measurement value and the updated sensor calibration factor(s) in lieu of the initial blood glucose reference measurement value and the initial sensor calibration factor(s) that were implemented prior to identifying the alert condition. In this manner, the closed-loop control is adaptive or otherwise responsive to a user's response to a previously generated user notification, such that closed-loop operation of the infusion device is provided or otherwise maintained after the alert condition was detected using different reference values and/or calibration factors when generating delivery commands.

Alternatively, if the updated blood glucose reference measurement value indicates an anomalous condition of the glucose sensing arrangement and/or the closed-loop control, another user notification may be generated that apprises the user of the anomalous condition and an alternative control of the infusion device is implemented. In a similar manner as described above, the anomalous condition user notification may also be generated in a user-specific manner in accordance with the individual user's alert configuration information. Similarly, if the updated blood glucose reference measurement value indicates a low blood glucose condition of the user, yet another user notification may be generated in accordance with the individual user's alert configuration information to apprise the user of the low blood glucose condition.

Turning now to FIG. 1, one exemplary embodiment of an infusion system 100 includes, without limitation, a fluid infusion device (or infusion pump) 102, a sensing arrangement 104, a command control device (CCD) 106, and a computing device (or computer) 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or U.S. patent application Ser. No. 13/966,120, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, such as, for example, only when the user is asleep (e.g., overnight). In this regard, in some embodiments, the closed-loop control may be implemented for a limited duration of time (e.g., an 8 hour time limit) before being disabled or otherwise unavailable for a threshold amount of time before the closed-loop control can be reinitiated.

Figure 2:
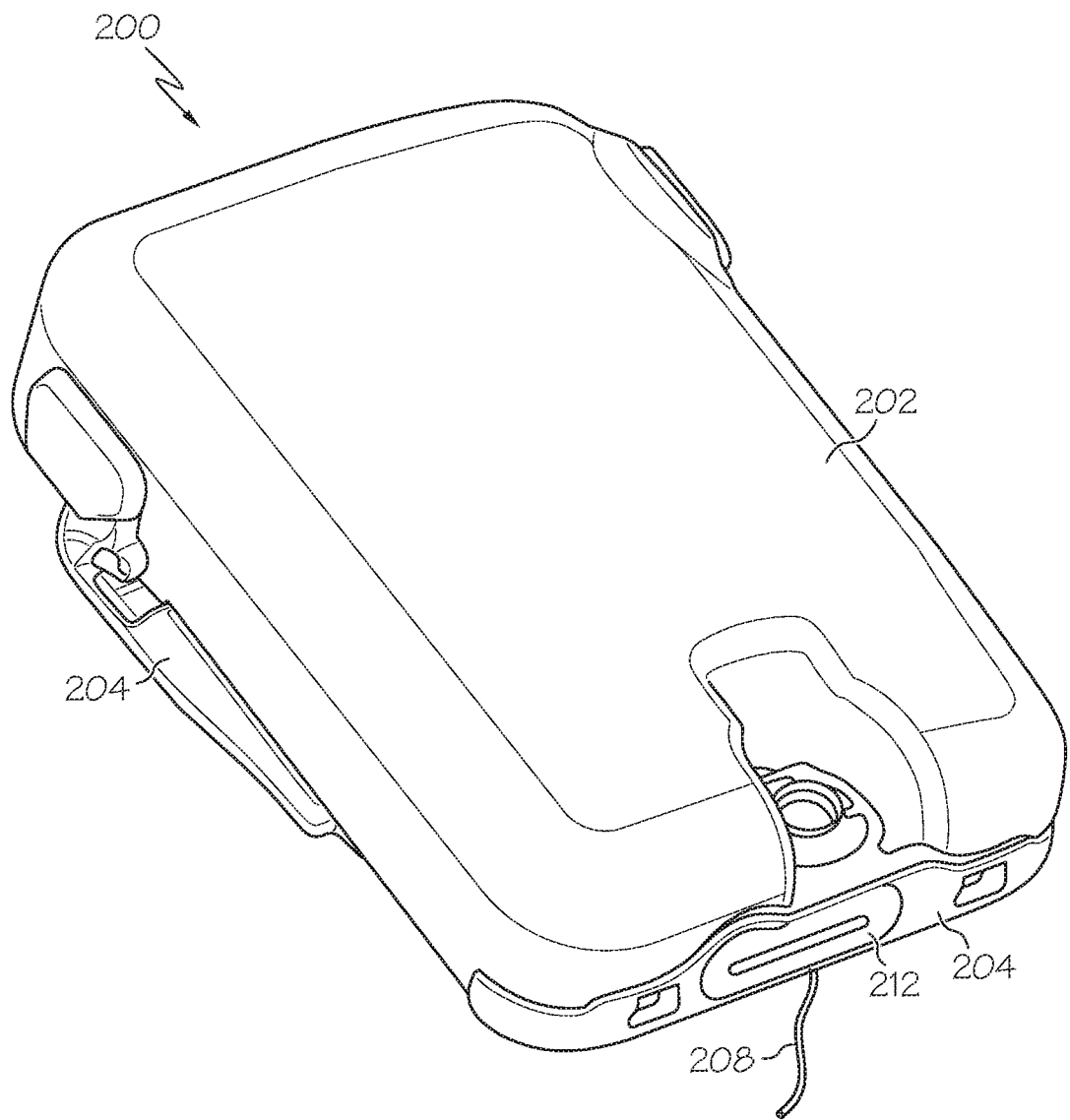
FIG. 2 is a perspective view of an exemplary embodiment of a fluid infusion device suitable for use in the infusion system of FIG. 1.
Figure 3:
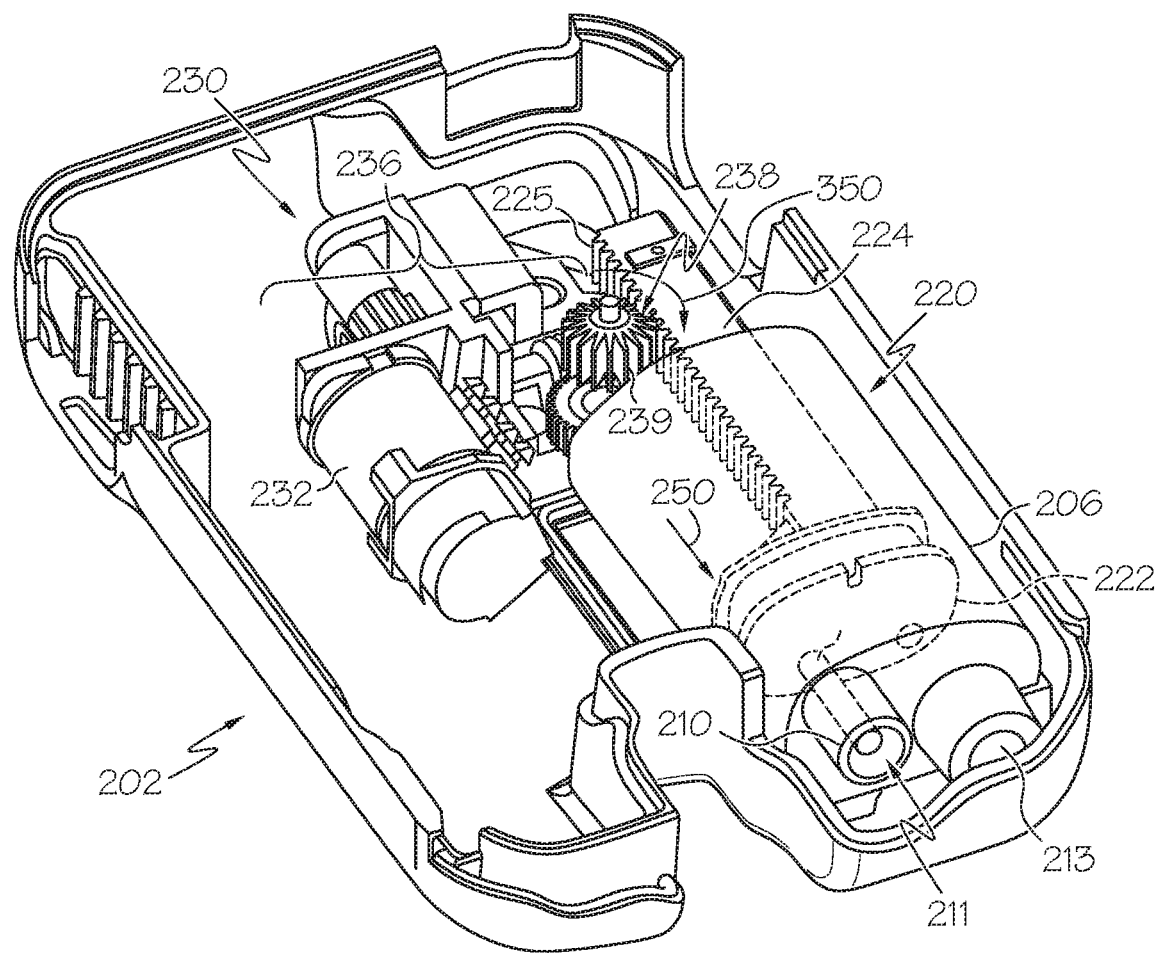
FIG. 3 is a perspective view that depicts the internal structure of the durable housing of the fluid infusion device shown in FIG. 2.

FIGS. 2-3 depict an exemplary embodiment of a fluid infusion device 200 suitable for use as the infusion device 102 in the infusion system 100 of FIG. 1. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate 204 is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. The durable housing 202 receives the fluid reservoir 206 and retains the fluid reservoir 206 in a substantially fixed position and orientation with respect to the durable housing 202 and the base place 204 while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal.

In exemplary embodiments, the fluid reservoir 206 includes a fluid delivery port 210 that cooperates with the reservoir port receptacle to establish a fluid delivery path. In this regard, the fluid delivery port 210 has an interior 211 defined therein that is shaped, sized, and otherwise configured to receive a sealing element when the fluid reservoir 206 is engaged with the reservoir port receptacle on base plate 204. The sealing element forms part of a sealing assembly for the fluid infusion device 200 and preferably includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208. In the illustrated embodiment, the fluid reservoir 206 includes a second fluid port for receiving fluid. For example, the second fluid port 213 may include a pierceable septum, a vented opening, or the like to accommodate filling (or refilling) of the fluid reservoir 206 by the patient, a doctor, a caregiver, or the like.

As illustrated in FIG. 3, the reservoir 206 includes a barrel 220 for containing fluid and a plunger 222 (or stopper) positioned to push fluid from inside the barrel 220 of the reservoir 206 along the fluid path through the cannula 208 to the user. A shaft 224 is mechanically coupled to or otherwise engages the plunger 222, and the shaft 224 has exposed teeth 225 that are configured to mechanically couple or otherwise engage the shaft 224 with a gear 238 of a drive system 230 contained in the durable housing 202. In this regard, the shaft 224 functions as a rack gear as part of a rack and pinion gear configuration. Although the subject matter may be described herein in the context of the shaft 224 being integral with or otherwise part of the plunger 222, in practice, the shaft 224 and the plunger 222 may be provided separately.

Various aspects of the motor drive system 230 may be similar to those described in U.S. patent application Ser. No. 13/049,803. The drive system 230 includes a motor 232 having a rotor that is mechanically coupled to a gear assembly 236 that translates rotation of the rotor to translational displacement the plunger 222 in the direction 250 of the fluid delivery port 210 to deliver fluid from the reservoir 206 to a user. Accordingly, the direction 250 may alternatively be referred to herein as the fluid delivery direction 250.

In exemplary embodiments, the motor 232 is realized as a DC motor, such as a stepper motor or brushless DC motor capable of precisely controlling the amount of displacement of the plunger 222 during operation of the infusion device 200. In exemplary embodiments, the rotor of the motor 232 is mechanically coupled to a rotary shaft, which, in turn, is mechanically coupled to a first gear of the gear assembly 236. For example, the first gear may be coaxial and/or concentric to and disposed about the rotary shaft, where the first gear is affixed to or otherwise integrated with the rotary shaft such that the first gear and the rotary shaft rotate in unison. The gear assembly 236 also includes a pinion gear 238 having exposed teeth 239 that are configured to mate with or otherwise engage the exposed teeth 225 on the shaft 224 when the reservoir 206 is seated in the durable housing 202, such that rotation or displacement of the pinion gear 238 in rotational delivery direction 350 produces a corresponding translational displacement of the shaft 224 and/or plunger 222 in the fluid delivery direction 250 to deliver fluid to the user.

During operation of the fluid infusion device 200, when the motor 232 is operated to rotate the rotor, the rotary shaft rotates in unison with the rotor to cause a corresponding rotation of the first gear, which, in turn, actuates the gears of the gear assembly 236 to produce a corresponding rotation or displacement of the pinion gear 238, which, in turn, displaces the shaft 224. In this manner, the rotary shaft translates rotation (or displacement) of the rotor into a corresponding rotation (or displacement) of the gear assembly 236 such that the teeth 239 of the pinion gear 238 apply force to the teeth 225 of the shaft 224 of the plunger 222 in the fluid delivery direction 250 to thereby displace the plunger 222 in the fluid delivery direction 250 and dispense, expel, or otherwise deliver fluid from the barrel 220 of the reservoir 206 to the user via the fluid delivery path provided by the cannula 208.

As described in greater detail below in the context of FIG. 7, in one or more exemplary embodiments, a motor position sensor (or rotor position sensor) is configured to measure, sense, or otherwise detect rotation (or displacement) of the rotary shaft and/or the rotor of the motor 232. The motor position sensor may be utilized to provide closed-loop control of the motor 232, such as, for example, as described in U.S. Pat. No. 8,603,026, the subject matter of which is hereby incorporated by reference in its entirety. In exemplary embodiments, the rotary shaft includes, is coupled to, or is otherwise associated with a detectable feature that is measurable or otherwise detectable by the motor position sensor. In this regard, the detectable feature may rotate in unison with the rotary shaft. In one or more embodiments, the motor position sensor is realized as an incremental position sensor configured to measure, sense, or otherwise detect incremental rotations of the rotary shaft and/or the rotor of the motor 232. For example, in accordance with one or more embodiments, the motor position sensor is realized as a rotary encoder.

Figure 4:
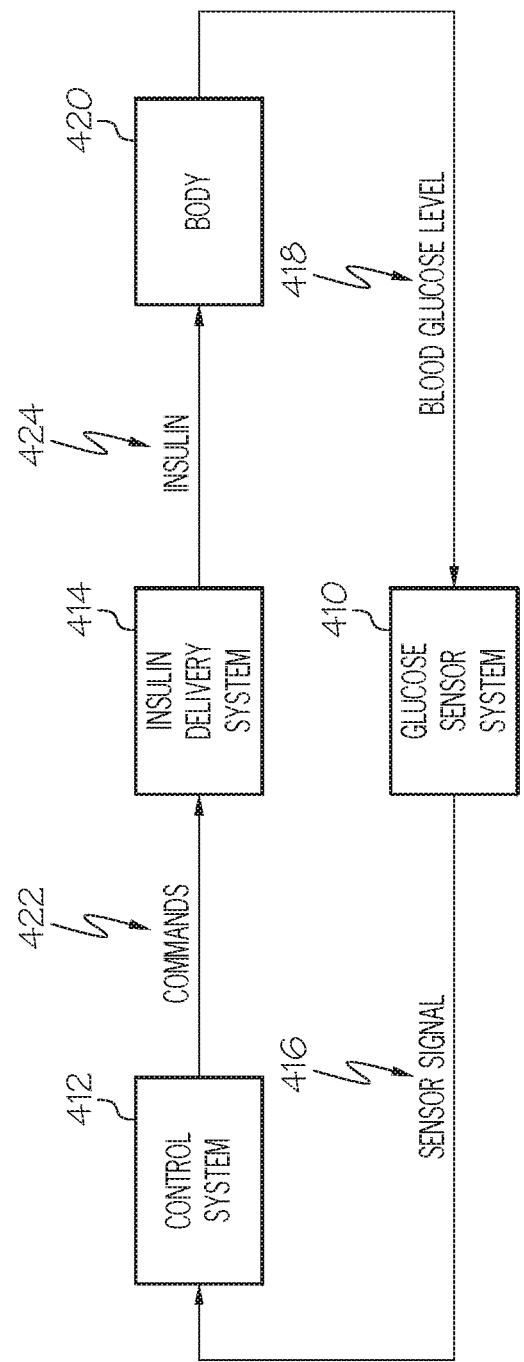
FIG. 4 is a block diagram of a closed-loop infusion system suitable for use with the infusion system of FIG. 1.

FIG. 4 depicts an exemplary embodiment of a closed-loop infusion system 400 suitable for use with or implementation by the infusion system 100 for regulating the rate of fluid infusion into a body of a user (e.g., by infusion device 102) based on feedback from an analyte concentration measurement taken from the body (e.g., via sensing arrangement 104). In exemplary embodiments, the infusion system 400 regulates the rate of insulin infusion into the body of a user based on a glucose concentration measurement taken from the body. In preferred embodiments, the infusion system 400 is designed to model a pancreatic beta cell (β-cell). In other words, the system controls the infusion device 102 to release insulin into a body of a user in a similar concentration profile as would be created by fully functioning human β-cells when responding to changes in blood glucose concentrations in the body. Thus, the infusion system 400 simulates the body's natural insulin response to blood glucose levels and not only makes efficient use of insulin, but also accounts for other bodily functions as well since insulin has both metabolic and mitogenic effects. However, the algorithms must model the β-cells closely, since algorithms that are designed to minimize glucose excursions in the body, without regard for how much insulin is delivered, may cause excessive weight gain, hypertension, and atherosclerosis. Thus, in some embodiments, the infusion system 400 is intended to emulate the in vivo insulin secretion pattern and to adjust this pattern consistent with the in vivo β-cell adaptation experienced by normal healthy individuals with normal glucose tolerance (NGT).

The illustrated closed-loop infusion system 400 includes a glucose sensor system 410, a control system 412 and an insulin delivery system 414. The glucose sensor system 410 (e.g., sensing arrangement 104) generates a sensor signal 416 representative of blood glucose levels 418 in the body 420, and provides the sensor signal 416 to the control system 412. The control system 412 receives the sensor signal 416 and generates commands 422 that are communicated to the insulin delivery system 414. The insulin delivery system 414 receives the commands 422 and infuses insulin 424 into the body 420 in response to the commands 422.

Generally, the glucose sensor system 410 includes a glucose sensor, sensor electrical components to provide power to the sensor and generate the sensor signal 416, a sensor communication system to carry the sensor signal 416 to the control system 412, and a sensor system housing for the electrical components and the sensor communication system.

Typically, the control system 412 includes controller electrical components and software to generate commands for the insulin delivery system 414 based on the sensor signal 416, and a controller communication system to receive the sensor signal 416 and carry commands to the insulin delivery system 414. In preferred embodiments, the control system 412 is housed in the infusion device housing (e.g., housing 202), however, in alternative embodiments, the control system 412 may be housed independently or in another component of an infusion system (e.g., the sensing arrangement 104, the CCD 106 and/or the computer 108).

The insulin delivery system 414 generally represents the infusion device (e.g., infusion device 102) and any other associated components for infusing insulin 424 into the body 420 (e.g., the motor 232, the gear assembly 236, and the like). In particular embodiments, the infusion device includes infusion electrical components to activate an infusion motor (e.g., motor 232) according to the commands 422, an infusion communication system to receive the commands 422 from the control system 412, and an infusion device housing (e.g., housing 202) to hold the infusion device.

Although not illustrated in FIG. 4, the closed-loop infusion system 400 may include or cooperate with a conventional blood glucose meter (e.g., a finger stick device) that provides measured blood glucose (BG) values to the control system 412 and/or to the insulin delivery system 414, such that the glucose sensor system 410 can be calibrated. For example, in certain embodiments, measured BG values are sent to the insulin delivery system 414, which in turn sends a measured BG value, sensor calibration factor, and calibration time to the control system 412. The control system 412 can process and analyze the received information to determine whether or not the infusion system 400 can enter the closed-loop operating mode. In this regard, the control system 412 may check to ensure that the calibration of the glucose sensor system 410 is within an acceptable range before allowing the system to enter the closed-loop mode.

In exemplary embodiments, after entering the closed-loop mode, the control system 412 receives, updates, or otherwise obtains sensor glucose (SG) values, sensor Isig values, calibration factors, "insulin delivered" values, and other data in accordance with a predetermined schedule, e.g., at five minute intervals. The control system 412 determines the desired insulin dose based on the closed-loop algorithm to maintain the patient at a target glucose setpoint, and communicates suitable control data and instructions to the insulin delivery system 414. The insulin delivery system 414 responds to deliver the insulin dose specified by the control system 412 to the user.

Referring to FIGS. 1-4, in one or more exemplary embodiments, the glucose sensor system 410 samples or otherwise obtains the sensor signal 416, stores the corresponding digital sensor values in a memory and then periodically transmits the digital sensor values from the memory to the control system 412. The control system 412 processes the digital sensor values and generates commands 422 for the insulin delivery system 414 to actuate the plunger 222 that forces insulin 424 out of the reservoir 206 the via a fluid communication path from the reservoir to the subcutaneous tissue of the user's body 420.

In preferred embodiments, the control system 412 is designed to model a pancreatic beta cell (β-cell). In other words, the control system 412 commands the infusion device 102, 200 to release insulin 424 into the body 420 at a rate that causes the insulin concentration in the blood to follow a similar concentration profile as would be caused by fully functioning human β-cells responding to blood glucose concentrations in the body 420.

Generally, the in vivo β-cell response to changes in glucose is characterized by "first" and "second" phase insulin responses. The biphasic insulin response of a β-cell can be modeled using components of a proportional, plus integral, plus derivative (PID) controller. Accordingly, the control system 412 may be realized as a PID controller since PID algorithms are stable for a wide variety of non-medical dynamic systems, and PID algorithms have been found to be stable over widely varying disturbances and changes in system dynamics.

A proportional component $U_P$ and a derivative component $U_D$ of the PID controller may be combined to represent a first phase insulin response, which lasts several minutes. An integral component $U_I$ of the PID controller represents a second phase insulin response, which is a steady increase in insulin release under hyperglycemic clamp conditions. As described in U.S. patent application Ser. No. 13/966,120, the magnitude of each component's contribution to the insulin response may be described by the following equations:

Proportional Component Response:

$$U_P = K_P(G - G_B)$$

Integral Component Response:

$$U_I = K_I \int_{t_0}^{t} (G - G_B) dt + I_B, \text{ and}$$

Derivative Component Response:

$$U_D = K_D \frac{dG}{dt},$$

Where $U_P$ is the proportional component of the command sent to the insulin delivery system, $U_I$ is the integral component of the command sent to the insulin delivery system, $U_D$ is the derivative component of the command sent to the insulin delivery system, $K_P$ is a proportional gain coefficient, $K_I$ is an integral gain coefficient, $K_D$ is a derivative gain coefficient, G is a present blood glucose level, $G_B$ is a desired basal glucose level, t is the time that has passed since the last sensor calibration, $t_0$ is the time of the last sensor calibration, and $I_B$ is a basal insulin concentration at to, or can also be described as $U_I(t_0)$.

As described in U.S. patent application Ser. No. 13/966, 120, the components of the PID controller can also be expressed in discrete form:

$$P_{con}^n = K_P(SG_f^n - G_{sp})$$

Proportional Component Response:
Integral Component Response:

$$I_{con}^n = I_{con}^{n-1} + K_I(SG_f^n - G_{sp}); I_{con}^0 = I_b$$

Derivative Component Response:

$$D_{con}^n = K_D dGdt_f^n$$

Where $K_P$, $K_I$, and $K_D$ are the proportional, integral, and derivative gain coefficients, $SG_f$ and $dGdt_f$ are the filtered sensor glucose and derivative respectively, and the superscript n refers to discrete time.

An acute insulin response is essential for preventing wide postprandial glycemic excursions. Generally, an early insulin response to a sudden increase in glucose level results in less total insulin being needed to bring the glucose level back to a desired basal glucose level. This is because the infusion of insulin increases the percentage of glucose that is taken up by the body. Infusing a large amount of insulin to increase the percentage of glucose uptake while the glucose concentration is high results in an efficient use of insulin. Conversely, infusing a large amount of insulin while the glucose concentration is low results in using a large amount of insulin to remove a relatively small amount of glucose. In other words, a larger percentage of a big number is more than a larger percentage of a small number. The infusion of less total insulin helps to avoid development of insulin resistance in the user. As well, first-phase insulin is thought to result in an early suppression of hepatic glucose output.

Insulin sensitivity is not fixed and can change dramatically in a body depending on the amount of exercise by the body. For example, the insulin response in an exercise-trained individual may be about one-half of the insulin response of an NGT individual, but the glucose uptake rate for the exercise-trained individual may be virtually identical to that of an NGT individual. Thus, an exercise-trained individual may have twice the insulin sensitivity and half of the insulin response leading to the same glucose uptake as an NGT individual. Not only is the first phase insulin response reduced due to the effects of exercise, but the second phase insulin response has also been shown to adjust to insulin sensitivity.

In preferred embodiments, a closed loop control system may be used for delivering insulin to a body to compensate for β-cells that perform inadequately. There is a desired basal blood glucose level $G_B$ for each body. The difference between the desired basal blood glucose level $G_B$ and an estimate of the present blood glucose level G is the glucose level error $G_E$ that must be corrected.

If the glucose level error $G_E$ is positive (meaning that the present estimate of the blood glucose level G is higher than the desired basal blood glucose level $G_B$) then the control system 412 generates an insulin delivery command 422 to drive the infusion device 102, 200 to provide insulin 424 to the body 420. In terms of the control loop, glucose is considered to be positive, and therefore insulin is negative. The sensing arrangement 104, 410 senses the interstitial fluid (ISF) glucose level and generates a sensor signal 416, which, in turn, may be filtered and calibrated to create an estimate of the present blood glucose level. In particular embodiments, the estimate of the present blood glucose level G is adjusted with correction algorithms before it is compared to the desired basal blood glucose level $G_B$ to calculate a new glucose level error $G_E$ to start the loop again.

If the glucose level error $G_E$ is negative (meaning that the present estimate of the blood glucose level is lower than the desired basal blood glucose level $G_B$) then the control system 412 reduces or stops the insulin delivery depending on whether the integral component response of the glucose error $G_E$ is still positive.

If the glucose level error $G_E$ is zero, (meaning that the present estimate of the blood glucose level is equal to the desired basal blood glucose level $G_B$) then the control system 412 may or may not issue commands to infuse insulin depending on the derivative component (whether the glucose level is raising or falling) and the integral component (how long and by how much glucose level has been above or below the basal blood glucose level $G_B$).

Figure 5:
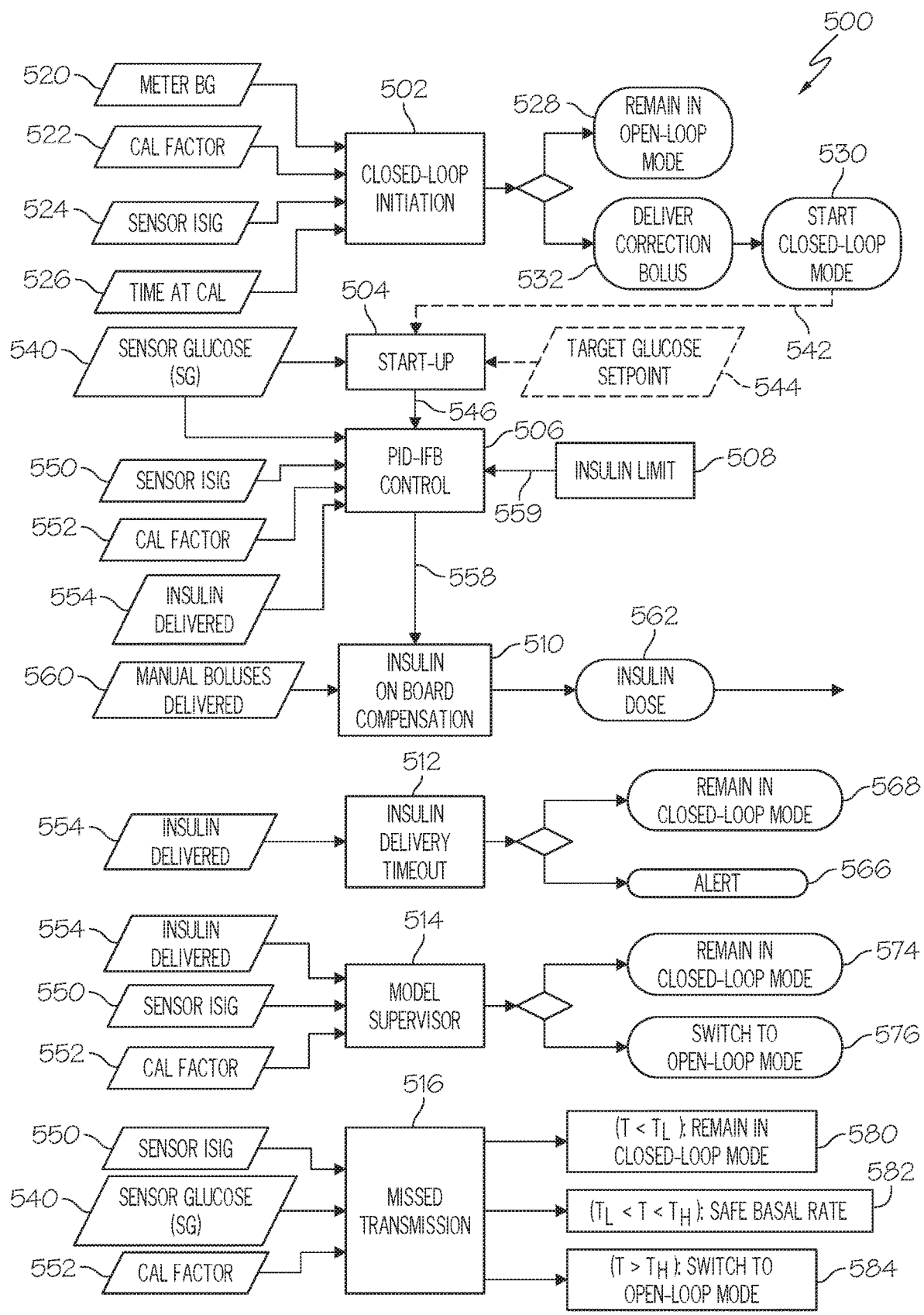
FIG. 5 is a block diagram that illustrates processing modules and algorithms of an exemplary embodiment of a control system suitable for use with the closed-loop infusion system of FIG. 4.
Figure 6:
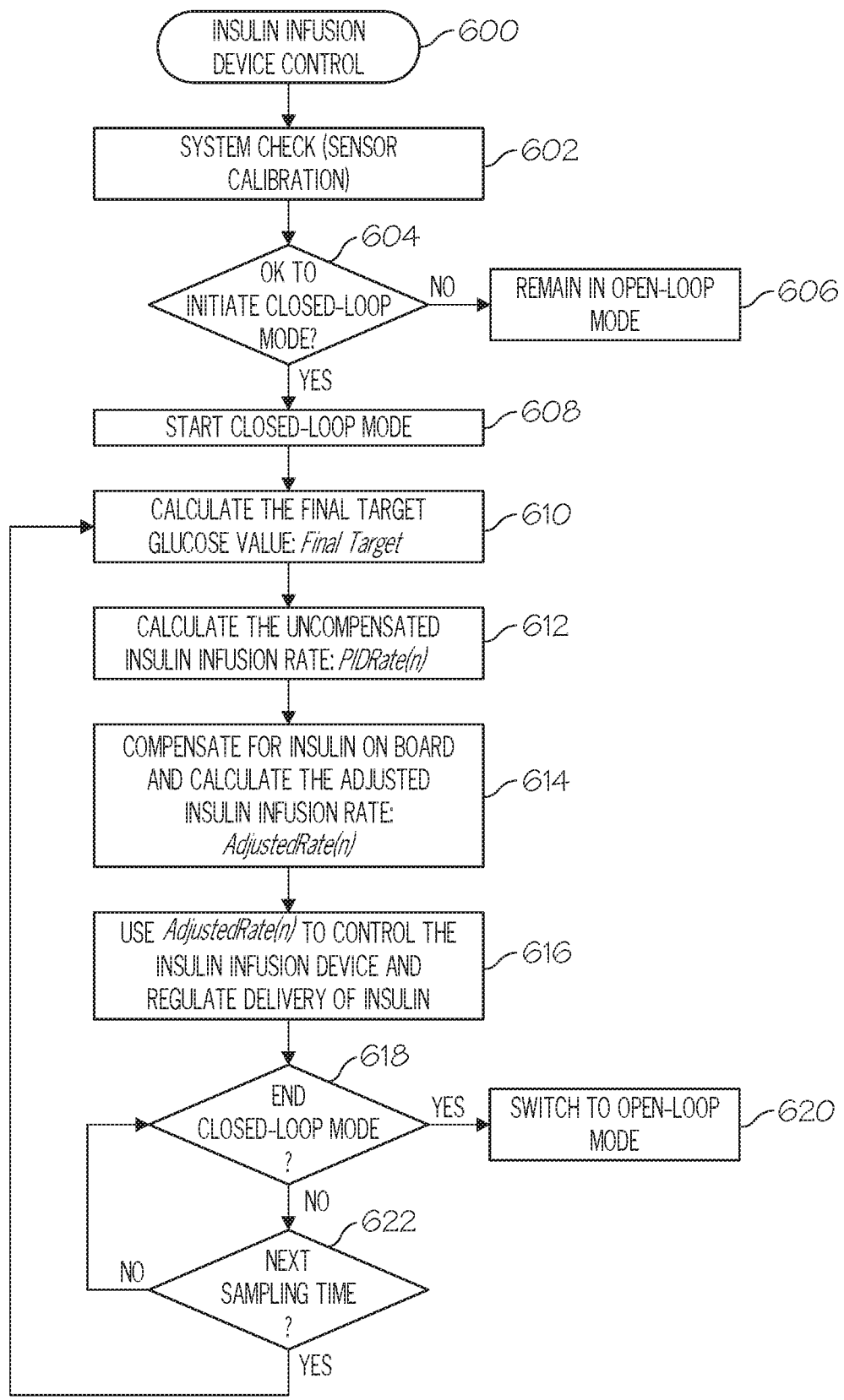
FIG. 6 is a flow diagram of an exemplary control process suitable for use with the control system of FIG. 5.

FIG. 5 depicts a block diagram that illustrates processing modules and algorithms of an exemplary embodiment of a control system 500 suitable for use as the control system 412 in the infusion system 400 of FIG. 4, and FIG. 6 is a flow chart that illustrates an exemplary embodiment of a control process 600 that may be performed at least in part by the control system 500 to control the insulin delivery system 414 (e.g., motor 232).

FIG. 5 schematically depicts certain inputs and outputs of the control system 500, where the parallelograms represent the inputs, the ovals represent the outputs, and the rectangles represent the various functional modules of the control system 500. In the context of this description, a "functional module" may be any process, technique, method, algorithm, computer-executable program logic, or the like. In this regard, the control system 500 could be realized as any electronic device having a processing architecture with at least one processor device, and at least one memory element that is cooperatively associated with the processing architecture. The processing architecture is suitably configured to execute processor-executable instructions stored in the at least one memory element such that the control system 500 can perform the various control operations and methods described in detail herein. Although FIG. 5 conveniently depicts a number of separate functional modules, it should be appreciated that the overall functionality and configuration of the control system 500 may be alternatively arranged, and that the functions, operations, and tasks described herein may be performed by one or more of the modules as needed.

The host electronic device that implements the control system 500 may be realized as a monitor device for an insulin infusion device, where the monitor device and the insulin infusion device are two physically distinct hardware devices. In another embodiment of the system, the host electronic device that implements the control system 500 may be realized as a portable wireless device, where the portable wireless device and the insulin infusion device are two physically distinct hardware devices. The portable wireless device in this context may be, without limitation: a mobile telephone device; a tablet computer device; a laptop computer device; a portable video game device; a digital media player device; a portable medical device; or the like. In yet other system embodiments, the host electronic device and the insulin infusion device are physically and functionally integrated into a single hardware device. In such embodiments, the insulin infusion device will include the functionality of the control system 500 as presented here.

Certain embodiments of the control system 500 include a plurality of cooperating functional modules that are designed and configured to determine the insulin dose to be delivered to keep the patient at the target glucose setpoint during an overnight closed-loop operating mode. In this regard, the illustrated embodiment of the control system 500 may include the following functional modules, without limitation: a closed-loop initiation module 502; a start-up module 504; a proportional integral derivative insulin feedback (PID-IFB) control module 506; an insulin limit module 508; an insulin on board (IOB) compensation module 510; an insulin delivery timeout module 512; a model supervisor module 514; and a missed transmission module 516.

Referring to FIG. 6, the control process 600 may begin at any time when it is desired to enter the closed-loop operating mode. Accordingly, the control process 600 may begin in response to a user-initiated command, automatically in response to the detection of operating conditions that are usually indicative of closed-loop operation (e.g., the user is sleeping), or the like. Certain embodiments of the control process 600 may begin with one or more system checks (task 602) to confirm whether or not the system is allowed to enter the closed-loop operating mode. This particular example employs a sensor calibration check before allowing the system to proceed to the closed-loop mode. Referring to FIG. 5, the closed-loop initiation module 502 may be involved during task 602.

In some embodiments, the closed-loop initiation module 502 may consider certain sensor performance criteria that prevents closed-loop initiation. Such criteria may include, without limitation: (1) during start-up when the calibration is not stable; (2) when the sensor sensitivity changes significantly; (3) when sensors may be calibrated with a potentially invalid meter reading thereby changing the sensor sensitivity significantly; (4) any other situation that could cause a mismatch between the sensor and meter for a number of most recent calibrations spaced over a designated period of time (e.g., the two most recent calibrations).

The illustrated embodiment of the closed-loop initiation module 502 receives at least the following items as inputs: a meter (measured) BG value 520; at least one sensor calibration factor 522 (i.e., calibration measurements, calibration data, etc.); the sensor Isig value 524; and timestamp data 526 that indicates the calibration time associated with the BG value 520 and the sensor calibration factor 522. Some or all of this input data may be provided directly or indirectly by the insulin delivery system 414 (see FIG. 4), a translator device, a monitor device, or any device in the closed-loop system. This description assumes that a new sensor calibration factor 522 and new timestamp data 526 may be generated for each meter BG value 520, wherein the sensor calibration factor 522 is associated with the calibration of the glucose sensor system 410 (see FIG. 4) that is being used to monitor the patient. In particular, the sensor calibration factor may be based on the meter BG value 520 and the corresponding sensor Isig value 524.

The closed-loop initiation module 502 analyzes the input data (both current values and historical values) to determine whether or not the system is allowed to enter into the closed-loop mode. For example, the closed-loop initiation module 502 may: check the period between two consecutive calibration timestamp values; compare recent and prior calibration factor values; and the like. The "outputs" of the closed-loop initiation module 502 correspond to two operating modes of the system. More specifically, the closed-loop initiation module 502 controls whether the system remains operating in the open-loop mode 528 or whether the system starts the closed-loop mode 530.

Referring to FIG. 6, if the closed-loop mode is not permitted (the "No" branch of query task 604), then the control process 600 operates the system such that it remains in the open-loop mode (task 606). On the other hand, if the closed-loop mode is permitted (the "Yes" branch of query task 604), then the control process 600 can initiate and start the closed-loop mode in an appropriate manner (task 608). Referring again to FIG. 5, a correction bolus 532 can be calculated and delivered (if needed) to mitigate hyperglycemia at the commencement of the closed-loop mode. This correction bolus 532 serves as an additional safeguard to achieve a target blood glucose level if a measured meter reading is greater than a threshold value. If the control process 600 determines that a correction bolus is required, then an appropriate insulin dose instruction is generated for execution by the insulin delivery system at the outset of the closed-loop mode.

Referring to FIG. 5, the start-up module 504 may be called in response to a determination that the system can proceed to the closed-loop operating mode. Once the system is in the closed-loop mode, the controller retrieves historical data that can be processed and used as described in more detail below. In one or more embodiments, for example, the controller obtains data for the last 24 hours (from the insulin delivery system, from a monitor, or the like). Thereafter, the controller retrieves data packets once every sampling period to obtain, without limitation: sensor glucose (SG) values; sensor Isig values; sensor calibration factors; information related to the amount of insulin delivered; information related to manual boluses delivered; and sensor calibration factors. As explained in more detail below, the received information can be used in the various safeguards, and to determine the final insulin dose.

The start-up module 504 receives sensor glucose (SG) values 540 as an input, and the functionality of the start-up module 504 may be initiated in response to the start of the closed-loop mode 530 (this trigger mechanism is represented by the dashed arrow 542 in FIG. 5). The SG values 540 may be provided directly by the glucose sensor system 410 or indirectly via the insulin delivery system 414, a translator device, or any device in the closed-loop system (see FIG. 4). This description assumes that SG values 540 are received by the start-up module 504 in an ongoing manner as they become available. The start-up module 504 may also utilize a target glucose setpoint value 544, which may be internally maintained, generated, and/or provided by the control system 500. For the implementation presented here, the target glucose setpoint value 544 represents a fixed (constant) value that the user can specify (FIG. 5 depicts the target glucose setpoint value 544 in dashed lines to indicate that the value is a user-specified parameter rather than a functional module or data received by the system).

In certain embodiments, the start-up module 504 calculates a final target glucose value 546, which serves as an input to the PID-IFB control module 506. The final target glucose value 546 enables the system to make a smoother transition between open-loop and closed-loop modes (by gradually adjusting the final target glucose value 546). The start-up module 504 may utilize the target glucose setpoint value 544 to calculate the final target glucose value 546. In this regard, the start-up module 504 elevates the final target glucose value 546 to the same level as the sensor glucose value at the start of the closed-loop mode, provided the sensor glucose is above a certain threshold. As time progresses, the final target glucose value 546 gradually decreases back to the target glucose setpoint value 544 (usually in approximately two hours). Referring to FIG. 6, the control process 600 calculates the final target glucose value (task 610) and continues by calculating an uncompensated insulin infusion rate, PIDRate(n), based at least in part on the final target glucose value (task 612). For this example, the start-up module 504 may be involved during task 610, and the PID-IFB control module 506 may be involved during task 612.

As an additional safeguard, the insulin limit module 508 cooperates with the PID-IFB control module 506 to provide an upper insulin limit that is calculated based on the patient's insulin intake during a designated fasting period, the patient's fasting blood glucose, and the patient's insulin sensitivity. This insulin limit imposes an upper limit to the insulin delivery rate to avoid over-delivery of insulin by the system due to potential sensor error.

The PID-IFB control module 506 may be configured to carry out the control processes described above with reference to FIG. 4. In some embodiments, the PID-IFB control module 506 receives at least the following items as inputs: the SG value 540 (which may be used to calculate a rate of change value that indicates the rate of change of the SG value); the current sensor Isig value 550; the current sensor calibration factor 552; and an amount of insulin delivered 554. As shown in FIG. 5, the PID-IFB control module 506 may also receive an insulin limit 559 (e.g., a maximum insulin infusion rate) for the user, as calculated by the insulin limit module 508. The inputs to the PID-IFB control module 506 may be provided directly or indirectly by the insulin delivery system 414, the glucose sensor system 410, a translator device, a monitor device, and/or any device in the closed-loop system (see FIG. 4). The PID-IFB control module 506 is suitably configured to calculate the insulin infusion rate based on the current and past SG values 540, the SG rate of change, the sensor Isig value 550, the sensor calibration factor 552, the final target glucose value 546, and the insulin delivered 554 in order to achieve euglycemia. These (and possibly other) values may be received by the PID-IFB control module 506 in an ongoing manner as they become available, e.g., in five minute intervals or in accordance with any desired schedule.

The insulin delivered 554 is a parameter or value that indicates the amount of insulin that has been delivered to the patient by the insulin delivery system. Thus, the insulin delivered 554 may indicate recent boluses (typically by Units) delivered over a period of time. In certain implementations, the insulin delivered 554 corresponds to the amount of insulin delivered in the last sampling time, which may be, without limitation: one minute; five minutes; thirty seconds; or any designated sampling time. The insulin delivered 554 may also indicate the amount of insulin delivered by the delivery system as basal or boluses in any defined period of time in the past (e.g., the last N hours) or the amount of insulin delivered by the system in the last sampling cycle. In practice, the PID-IFB control module 506 (and the IOB compensation module 510) may be "initialized" to collect and save historical values for the insulin delivered 554 as needed. Thereafter, the insulin delivered 554 can simply indicate an amount of insulin administered by the system during the last sampling time period if by a bolus or basal channels.

As mentioned above, the PID-IFB control module 506 may utilize the upper insulin limit 559, which is a patient-specific parameter. In certain embodiments, the upper insulin limit 559 may be entered by the user, a caregiver, or the like. Alternatively, the insulin limit module 508 may be responsible for calculating or otherwise managing the upper insulin limit 559 if so desired. The upper insulin limit 559 imposes an upper limit to the insulin delivery rate as an additional safety feature to avoid over-delivery of insulin by the control system 500 due to potential sensor error. Thus, if the PID-IFB control module 506 recommends a dose higher than the insulin limit 559, the insulin limit 559 will be utilized to constrain the insulin delivered to the insulin limit value. In addition, implementation of the insulin limit 559 will "freeze" the integral component of the PID to its previous value to prevent integral windup, which can cause continuous integrating of the glucose error until it reaches maximum values. In certain embodiments, the upper insulin limit 559 has a default value set at five times the patient's basal rate. Hence, if the maximum value is reached, the PID-IFB control algorithm will be fairly aggressive in calculating an insulin dose. Accordingly, to minimize integral windup, the insulin limit 559 is fed back to the PID-IFB control module 506 (as depicted in FIG. 5) for use in the next insulin dose calculation.

The PID-IFB control module 506 operates as described previously to calculate a current insulin dose 558 as an output value (the current insulin dose 558 is also referred to herein as the uncompensated insulin infusion rate, PIDRate (n)). In practice, the current insulin dose 558 is typically expressed as an infusion rate (Units/Hour). In the context of this description, the current insulin dose 558 may represent a closed-loop infusion rate that has already been subjected to limiting by the insulin limit module 508, and which may be subjected to further adjustment or compensation by the IOB compensation module 510. Thus, the output of the insulin limit module 508 (the upper insulin limit 559) represents a potentially limited insulin dose to be provided by the PID-IFB control module 506—if no limit is imposed, then the insulin limit 559 has no effect on the output of the PID-IFB control module 506; otherwise, the current insulin dose 558 will be the same as the upper insulin limit 559. Referring again to FIG. 6, the control process 600 may compensate for the insulin "on board" the patient by calculating an adjusted insulin infusion rate, AdjustedRate(n), based at least in part on the uncompensated insulin infusion rate (task 614). For this example, the IOB compensation module 510 may be involved during task 614.

The IOB compensation module 510 receives at least the following items as inputs: the current insulin dose 558; and information regarding manual boluses delivered 560. The manual boluses delivered 560 may be provided directly or indirectly by the insulin delivery system 414, a translator device, a monitor device, and/or any device in the closed-loop system (see FIG. 4). This description assumes that the manual boluses delivered 560 is received by the IOB compensation module 510 in an ongoing manner as it becomes available, e.g., in five minute intervals or in accordance with any desired schedule. The IOB compensation module 510 is suitably configured to estimate insulin on board based on manual boluses delivered, before or during closed-loop operation, in order to compensate the final infusion rate to help avoid over-delivery of insulin by the control system 500. Accordingly, the output of the IOB compensation module 510 may be a final insulin dose 562 expressed as a final infusion rate (Units/Hour). The final insulin dose 562 is also referred to herein as the adjusted insulin infusion rate, AdjustedRate(n).

Referring to FIG. 6, the control process 600 uses the adjusted insulin infusion rate, AdjustedRate(n), to control the insulin infusion device, which in turn regulates the delivery of insulin to the body of the user (task 616). In certain embodiments, the adjusted insulin infusion rate is communicated to the insulin infusion device in an appropriate manner (such as wireless data communication). The control process 600 may continue as described above in an iterative and ongoing manner to monitor the condition of the user and deliver insulin as needed without user involvement. That said, if the control process 600 determines that the closed-loop operating mode should be terminated (the "Yes" branch of query task 618), then the control process 600 causes the system to switch back to the open-loop mode (task 620). The closed-loop mode may be ended in response to a user-initiated command, automatically in response to the detection of operating conditions that are usually indicative of open-loop operation, or the like.

If query task 618 determines that the closed-loop mode should continue (the "No" branch of query task 618), then the control process 600 may check whether it is time to perform another iteration of the control routine. In other words, the control process 600 may check for the next sampling time (query task 622). If it is time for the next iteration, then the control process 600 may return to task 610 and repeat the computations with the next set of data values. For example, the next iteration of the control routine may obtain and process the current values of some or all of the following parameters, without limitation: the SG value 540; the SG rate of change; the sensor Isig value 524; the amount of insulin delivered 554; and the manual boluses delivered 560. This allows the control process 600 to adjust the final insulin infusion rate in an ongoing manner in accordance with a predetermined schedule, a designated sampling rate, or the like.

The insulin delivery timeout module 512 monitors if the patient is receiving continuous delivery of insulin at the maximum insulin limit or the minimum allowable infusion of zero Units/Hour for a time specified by the controller. Accordingly, the insulin delivery timeout module 512 may receive the insulin delivered 554 as an input. If the specified time is exceeded, the system will trigger a fail-safe alert 566. Otherwise, the system remains in the closed-loop operating mode 568.

Referring back to FIG. 5, the model supervisor module 514 receives at least the following as inputs: the insulin delivered 554; sensor Isig values 550; and one or more sensor calibration factors 552. The inputs to the model supervisor module 514 may be provided directly or indirectly by the insulin delivery system 414, the glucose sensor system 410, a translator device, a monitor device, and/or any device in the closed-loop system (see FIG. 4). The model supervisor module 514 is suitably designed and configured to estimate the user's glucose concentration in real time (or substantially real time) based on the insulin delivered 554, the sensor Isig values 550, and the sensor calibration factors 552. The sensor calibration factors 552 used by the model supervisor module 514 are equal to the sensor calibration factors 522 used by the closed-loop initiation module 502. That said, the closed-loop initiation module 502 utilizes the sensor calibration factors 522 at one particular time, whereas the model supervisor module 514 considers the sensor calibration factors 552 in an ongoing and continuous manner during operation in the closed-loop mode. Should the model-predicted glucose and the sensor glucose values differ significantly, the system will exit closed loop mode. Accordingly, the model supervisor module 514 regulates whether the system remains in the closed-loop mode 574 or switches to the open-loop mode 576.

The missed transmission module 516 is suitably configured to monitor the following, without limitation: the sensor Isig values 550; the SG values 540; and the sensor calibration factors 552. More particularly, the missed transmission module 516 continuously monitors to check whether the system is receiving data packets that convey the necessary information and input values. For missed data packets totaling less than a lower threshold of time (e.g., 15 minutes), the system remains in the closed-loop mode, as indicated by block 580 in FIG. 5. During this time, the system will continue to calculate the insulin dose using the closed-loop control methodology based on the last valid sensor glucose value. For missed data packets totaling a time longer than the lower threshold and shorter than an upper threshold of time (e.g., 60 minutes), the missed transmission module 516 will switch the system to a pre-programmed safe basal rate, as indicated by block 582 in FIG. 5. In certain embodiments, this safe basal rate is defined as half the patient's overnight basal rate, and this parameter may be programmed by a caregiver or physician. If the missed transmission module 516 starts receiving data packets while the safe basal rate is being administered, the system will switch back to the closed-loop mode. For missed data packets totaling more than the upper threshold of time, the system will switch to the open-loop mode, as indicated by block 584 in FIG. 5. At this point, the system will be controlled to deliver a pre-programmed open-loop overnight basal rate.

To summarize, the control system 500 determines whether to enter into the closed-loop mode in response to at least the recent meter BG values 520, the sensor calibration factors 522, and the calibration timestamp data 526. The control system 500 utilizes the closed-loop initiation module 502 to check if the sensor calibration time between the last two calibration values is within an acceptable range, and whether any change between the two calibration values (recent and prior value) is acceptable. If so, the control system 500 will switch the system into the closed-loop mode. Once the system is in the closed-loop mode, the control system 500 will periodically receive data packets (e.g., every five minutes) that include the current SG value 540, the current sensor Isig values 550, the insulin delivered 554, the sensor calibration factors 552, and manual boluses delivered 560. In certain embodiments, each of the data packets received by the control system 500 includes data collected during the previous 24-hour period.

The start-up module 504 utilizes the SG values 540 and the target glucose setpoint value 544 to calculate the final target glucose value 546. In some embodiments, the target glucose setpoint value 544 is set to 120 mg/dL, although other settings could be used if so desired (a typical range of settings may be, for example 70-300 mg/dL). This results in a smoother transition between open-loop and closed-loop modes by gradually adjusting the final target glucose value 546. The final target glucose value 546 is sent to the PID-IFB control module 506 for use as one input that influences the calculation of the final insulin dose 562.

The PID-IFB control module 506 utilizes the final target glucose value 546, the current and past SG values 540, the SG rate of change values, and the insulin delivered 554 to determine the insulin infusion rate (the current insulin dose 558) in order to achieve euglycemia. As an additional safeguard, the upper insulin limit 559 (calculated based on the patient's insulin intake during a fasting period, fasting blood glucose, and insulin sensitivity) from the insulin limit module 508 is input into the control system 500 for each patient to impose an upper limit to the insulin delivery rate to avoid over-delivery of insulin by the control system 500. The PID-IFB control module 506 considers the upper insulin limit 559 before sending the current insulin dose 558 to the IOB compensation module 510, which estimates insulin on board from manual boluses, before or during closed-loop operation, in order to calculate the final insulin dose 562. The final insulin dose 562 may be communicated from the control system 500 directly or indirectly to the insulin delivery system 414 such that the final insulin dose 562 can be delivered to the patient during closed-loop operation.

Additional safeguards could be implemented to monitor the system during closed-loop operation, such that the system exits the closed-loop mode when certain criteria are not met. For example, the control system 500 may cause the system to exit the closed-loop mode if more than a designated number of consecutive data packets are missed. This assumes that the control system 500 usually receives data packets (from the insulin delivery system 414, from a monitor, from a translation device, or the like) in a continuous manner during closed-loop operation. Thus, if the control system 500 detects that more than a threshold number of consecutive data packets are not received as expected, the system will be commanded to exit the closed-loop mode. This functionality is associated with the missed transmission module 516, as described previously.

Moreover, the model supervisor module 514 estimates the user's glucose concentration in an ongoing manner, based on the insulin delivered 554, the sensor Isig values 550, and the sensor calibration factors 552. If the difference between the model-predicted glucose and the sensor glucose value is greater than a stated threshold, the control system 500 may cause the system to exit the closed-loop mode.

As summarized above, the control system 500 employs a number of modules or functions that cooperate to regulate the delivery of insulin during closed-loop operation: the closed-loop initiation module 502; the start-up module 504; the PID-IFB control module 506; the insulin limit module 508; and the IOB compensation module 510. Moreover, the control system 500 may employ a number of modules that perform various safeguarding functions during closed-loop operation. These safeguarding modules may include: the insulin delivery timeout module 512; the model supervisor module 514; and the missed transmission module 516.

Figure 7:
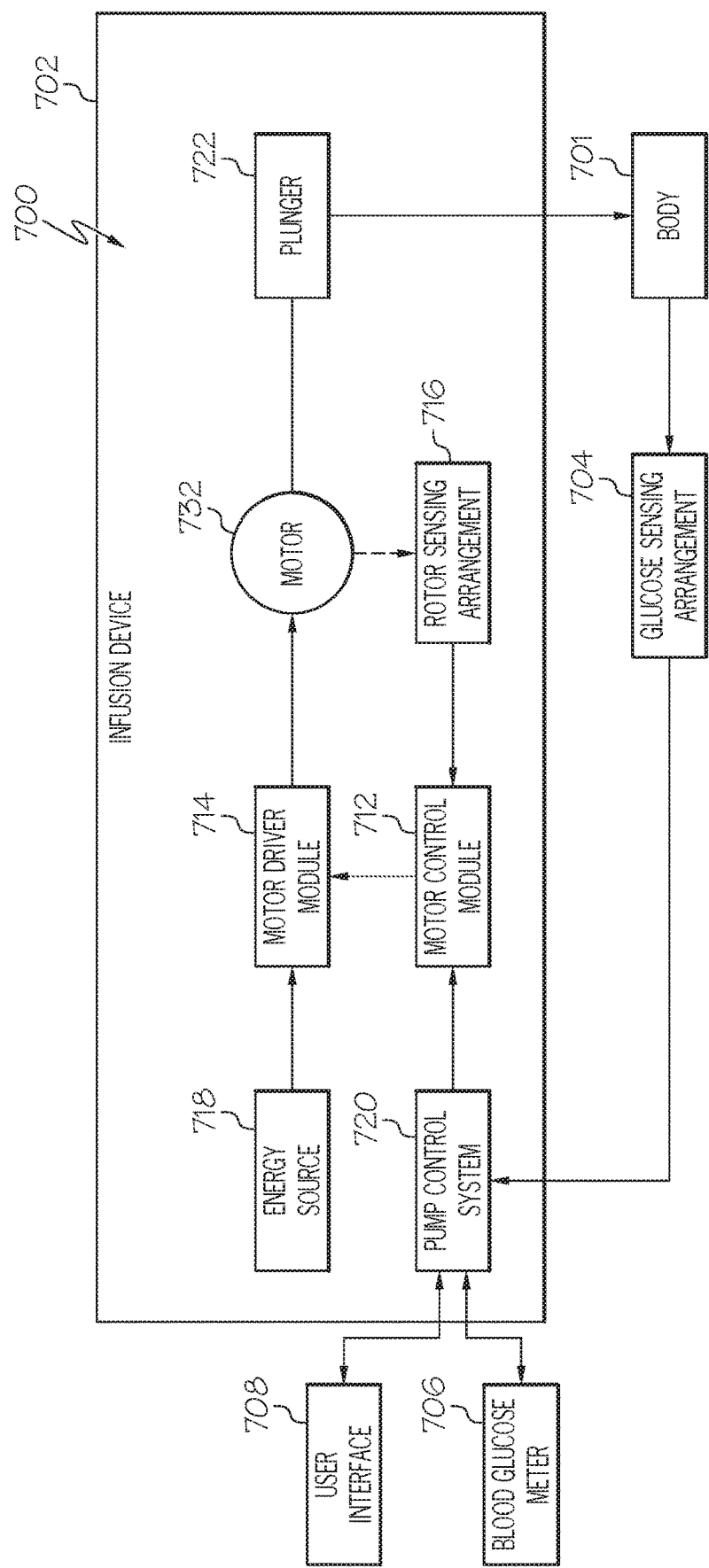
FIG. 7 is a block diagram of an exemplary infusion system suitable for use with the closed-loop infusion system of FIGS. 4-6.

FIG. 7 depicts another exemplary embodiment of an infusion system 700 suitable for use with an infusion device 702, such as the infusion device 102 in FIG. 1 or the infusion device 200 of FIG. 2 in conjunction with the closed-loop infusion system 400 of FIG. 4 and the closed-loop control process 600 of FIG. 6. In this regard, the illustrated infusion system 700 is capable of operating the infusion device 702 to control or otherwise regulate a condition in the body 701 of a user, such as the blood glucose level, to a desired (or target) value or otherwise maintain the condition within a range of acceptable values. In exemplary embodiments, a sensing arrangement 704 (e.g., sensing arrangement 104) communicatively coupled to the infusion device 702 is configured to sense, detect, measure or otherwise quantify the condition being regulated in the body 701 of the user. However, it should be noted that in alternative embodiments, the condition being regulated by the infusion system 700 may be correlative to the measured values obtained by the sensing arrangement 704. That said, for clarity and purposes of explanation, the subject matter may be described herein in the context of the sensing arrangement 704 being realized as an interstitial glucose sensing arrangement that senses, detects, measures or otherwise quantifies the interstitial fluid glucose level, which is being regulated in the body 701 of the user. As used herein, sensor glucose value, sensed glucose value, and variants thereof should be understood as referring to the quantified interstitial fluid glucose level that is either output by the sensing arrangement 704 or determined based on the output of the sensing arrangement 704.

In exemplary embodiments, the infusion system 700 includes a meter 706 that is configured to directly sense, detect, measure or otherwise quantify the condition in the body 701 of the user that is being regulated by the infusion device 702. For example, the infusion system 700 may include a blood glucose meter 706, such as a finger stick device, that directly senses, detects, measures or otherwise quantifies the user's blood glucose level and outputs or otherwise provides the measured blood glucose value (e.g., measured BG value 520). In this regard, the blood glucose meter 706 may provide a reliable measurement of the user's blood glucose level that may be used as a reference measurement when calibrating the interstitial glucose sensing arrangement 704 and/or providing closed-loop control of the user's blood glucose level.

In the illustrated embodiment, the pump control system 720 generally represents the electronics and other components of the infusion device 702 that control operation of the fluid infusion device 702 according to a desired infusion delivery program in a manner that is influenced by sensor data pertaining to a condition of a user (e.g., the user's current glucose level) received from the glucose sensing arrangement 704 and/or in a manner that is dictated by the user. To support closed-loop control, the pump control system 720 maintains, receives, or otherwise obtains a desired value for a condition in the body 701 of the user to be regulated (e.g., a target or commanded glucose value). For example, the infusion device 702 may store or otherwise maintain the target value in a data storage element accessible to the pump control system 720. Alternatively, the target value may be received from an external component (e.g., CCD 106 and/or computer 108) or be input by a user via a user interface element 708 associated with the infusion device 702.

As described in greater detail below in the context of FIGS. 9-10, in exemplary embodiments, the pump control system 720 is coupled to one or more user interface elements 708 to receive or otherwise obtain alert configuration information for the user associated with the infusion device 702 and generate or otherwise provide notifications to the user in accordance with that user's alert configuration while operating the infusion device 702 to provide closed-loop control of the user's blood glucose level. In this regard, to receive the user's alert configuration information, the one or more user interface element(s) 708 include at least one input user interface element, such as, for example, a button, a keypad, a keyboard, a knob, a joystick, a mouse, a touch panel, a touchscreen, a microphone or another audio input device, and/or the like. Similarly, to generate user notifications according to the user's alert configuration information, the one or more user interface element(s) 708 include at least one output user interface element, such as, for example, a display element (e.g., a light-emitting diode or the like), a display device (e.g., a liquid crystal display or the like), a speaker or another audio output device, a haptic feedback device, or the like. It should be noted that although FIG. 7 depicts the user interface element(s) 708 as being separate from the infusion device 702, in practice, one or more of the user interface element(s) 708 may be integrated with the infusion device 702. Additionally, in various embodiments, one or more of the user interface element(s) 708 may be integrated in another component of the infusion system 700 (e.g., the CCD 106, the computer 108, or the like) that is communicatively coupled to the infusion device 702 and/or the pump control system 720 as described above in the context of FIG. 1. In such embodiments, the pump control system 720 may support remote user notifications (e.g., text messages, e-mails, or the like) that are provided to the user or other individuals designated by the user as desired by the user and indicated by the user's alert configuration information.

In exemplary embodiments, the pump control system 720 stores or otherwise maintains the user's alert configuration information and accesses the user's alert configuration information in conjunction with providing closed-loop control of the user's blood glucose as described above in the context of FIGS. 4-6. In this regard, when the pump control system 720 detects or otherwise identifies a potential alert condition (e.g., an insulin delivery timeout, a deviation in an estimated or predicted sensor glucose value relative to the current sensor glucose value from the glucose sensing arrangement 704, a missed transmission, or the like) while providing closed-loop control, the pump control system 720 consults the user's alert configuration information to determine whether the user wants to be notified (or the user wants others to be notified) of that condition, and if so, the manner in which the user wants to be notified of that condition. Thereafter, the pump control system 720 automatically generates or otherwise provides the desired user notification(s) for the detected alert condition to the user via the one or more user interface element(s) 708. For example, a user's alert configuration information may indicate that the user would like to be provided with only a visual notification (e.g., a flashing light or another indicator) when the missed transmission module 516 detects missed data packets totaling a time shorter than an upper threshold of time, and that the user would like to be provided with both auditory and haptic feedback when the missed transmission module 516 detects missed data packets totaling a time longer than the upper threshold of time that results in transitioning to the open-loop overnight basal rate delivery mode. Thus, when the pump control system 720 detects missed transmissions for a duration of time that is less than the upper threshold, the pump control system 720 may illuminate or otherwise operate a display element 708 to provide a visual notification of the missed transmission to the user, and thereafter operate an audio output device 708 and a haptic feedback device 708 to provide auditory and haptic notifications to the user upon detecting that the missed transmissions exceed the upper threshold. In this manner, the user may be apprised of different alert conditions in different manners, and the manner in which one user is notified of the various different alert conditions may be different from other users. Thus, the alert configuration information may be understood as being user-specific, in that it may be unique to the user associated with the infusion device 702.

As described in greater detail below in the context of FIGS. 9-10, in response to a user notification generated by the pump control system 720, the user may respond or otherwise interact with the pump control system 720 and/or the infusion device 702 to provide a user response to the notification that influences subsequent operation of the infusion device 702. For example, in response to a user notification, the user may operate the blood glucose meter 706 to provide an updated (or new) blood glucose measurement to the pump control system 720 which may be utilized as a blood glucose reference measurement for recalibrating the glucose sensing arrangement 704 and/or reinitializing the closed-loop control. In other embodiments, the user may manipulate or otherwise operate an input user interface element 708 to modify or otherwise adjust settings or other configuration information for the infusion device 702 that influences subsequent operation of the infusion device 702 (e.g., changing the safe basal rate, the overnight basal rate, or the like). Thus, not only may the user notification be generated in a user-specific manner, but each individual user may respond to a particular user notification in a different manner based on that user's personal preferences or other factors, thereby allowing the user to further personalize or otherwise influence the manner in which the closed-loop control is subsequently implemented by the infusion device 702 and/or the pump control system 720.

Still referring to FIG. 7, the infusion device 702 includes a motor control module 712 coupled to a motor 732 (e.g., motor 232) that is operable to displace a plunger 722 (e.g., plunger 222) in a reservoir (e.g., reservoir 206) and provide a desired amount of fluid to the body 701 of a user. In this regard, displacement of the plunger 722 results in the delivery of a fluid that is capable of influencing the condition in the body 701 of the user via the body 701 of the user via a fluid delivery path. A motor driver module 714 is coupled between an energy source 718 and the motor 732. The motor control module 712 is coupled to the motor driver module 714, and the motor control module 712 generates or otherwise provides command signals that operate the motor driver module 714 to provide current (or power) from the energy source 718 to the motor 732 to displace the plunger 722 in response to receiving, from a pump control system 720, a delivery command (or dosage command) indicative of the desired amount of fluid to be delivered.

In exemplary embodiments, the energy source 718 is realized as a battery housed within the infusion device 702 (e.g., within housing 202) that provides direct current (DC) power. In this regard, the motor driver module 714 generally represents the combination of circuitry, hardware and/or other electrical components configured to convert or otherwise transfer DC power provided by the energy source 718 into alternating electrical signals applied to respective phases of the stator windings of the motor 732 that result in current flowing through the stator windings that generates a stator magnetic field and causes the rotor of the motor 732 to rotate. The motor control module 712 is configured to receive or otherwise obtain a delivery command (or commanded dosage) from the pump control system 720, convert the delivery command to a commanded translational displacement of the plunger 722, and command, signal, or otherwise operate the motor driver module 714 to cause the rotor of the motor 732 to rotate by an amount that produces the commanded translational displacement of the plunger 722. For example, the motor control module 712 may determine an amount of rotation of the rotor required to produce translational displacement of the plunger 722 that achieves the commanded dosage received from the pump control system 720.

Based on the current rotational position (or orientation) of the rotor with respect to the stator that is indicated by the output of the rotor sensing arrangement 716, the motor control module 712 determines the appropriate sequence of alternating electrical signals to be applied to the respective phases of the stator windings that should rotate the rotor by the determined amount of rotation from its current position (or orientation). In embodiments where the motor 732 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 712 operates the motor driver module 714 to apply the determined alternating electrical signals (e.g., the command signals) to the stator windings of the motor 732 to achieve the desired delivery of fluid to the user. When the motor control module 712 is operating the motor driver module 714, current flows from the energy source 718 through the stator windings of the motor 732 to produce a stator magnetic field that interacts with the rotor magnetic field. In some embodiments, after the motor control module 712 operates the motor driver module 714 and/or motor 732 to achieve the commanded dosage, the motor control module 712 ceases operating the motor driver module 714 and/or motor 732 until a subsequent delivery command is received. In this regard, the motor driver module 714 and the motor 732 enter an idle state during which the motor driver module 714 effectively disconnects or isolates the stator windings of the motor 732 from the energy source 718. In other words, current does not flow from the energy source 718 through the stator windings of the motor 732 when the motor 732 is idle, and thus, the motor 732 does not consume power from the energy source 718 in the idle state, thereby improving efficiency.

Depending on the embodiment, the motor control module 712 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 712, or in any practical combination thereof. In exemplary embodiments, the motor control module 712 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 712. The computer-executable programming instructions, when read and executed by the motor control module 712, cause the motor control module 712 to perform the tasks, operations, functions, and processes described herein.

It should be understood that FIG. 7 depicts a simplified representation of the infusion device 702 for purposes of explanation and is not intended to limit the subject matter described herein in any way. In this regard, depending on the embodiment, some features and/or functionality of the motor control module 712 may implemented by or otherwise integrated into the pump control system 720, or vice versa. Furthermore, some of the features and/or functionality of the pump control system 720 described herein may be implemented by a remote computing device that is physically distinct and/or separate from the infusion device 702 (e.g., the CCD 106, the computer 108, and/or another monitor device) and communicatively coupled to the motor control module 712, the sensing arrangement 704 and/or the blood glucose meter 706. Additionally, although FIG. 7 depicts the glucose sensing arrangement 704 as being physically separate and distinct from the infusion device 702, in alternative embodiments, the glucose sensing arrangement 704 may be integrated into or otherwise implemented by the infusion device 702 (e.g., by providing the glucose sensing arrangement 704 within the housing 202).

Figure 8:
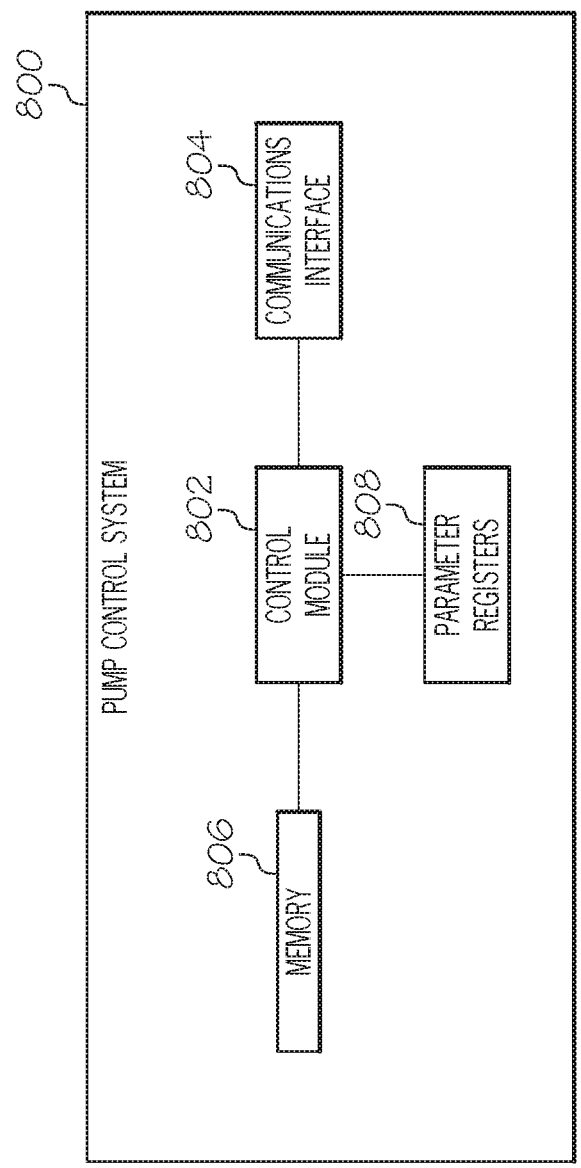
FIG. 8 is a block diagram of an exemplary pump control system suitable for use in the infusion system of FIG. 7.

FIG. 8 depicts an exemplary embodiment of a pump control system 800 suitable for use as the pump control system 720 in FIG. 8 in accordance with one or more embodiments. The illustrated pump control system 800 includes, without limitation, a pump control module 802, a communications interface 804, and data storage elements 806, 808. It should be understood that FIG. 8 is a simplified representation of pump control system 800 for purposes of explanation and is not intended to limit the subject matter described herein in any way. In this regard, although FIG. 8 depicts the data storage elements 806, 808 as being distinct or otherwise separate from one another, in practice, the data storage elements 806, 808 may be realized using a single integrated data storage element.

The control module 802 generally represents the hardware, circuitry, logic, firmware and/or other components of the pump control system 800 configured to determine delivery (or dosage) commands for operating a motor using closed-loop control and perform various additional tasks, operations, functions and/or operations described herein. Depending on the embodiment, the control module 802 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 802, or in any practical combination thereof.

The communications interface 804 generally represents the hardware, circuitry, logic, firmware and/or other components configured to support communications to/from the pump control system 800. For example, referring to FIGS. 1 and 7, the communications interface 804 may include or otherwise be coupled to one or more transceiver modules capable of supporting wireless communications between the infusion device 702 and another device (e.g., one or more of the sensing arrangements 104, 704, the blood glucose meter 706, the CCD 106, the computer 108, or the like).

In exemplary embodiments, the data storage element (or memory) 806 is realized as any sort of random access memory (RAM), read only memory (ROM), flash memory, registers, hard disks, removable disks, magnetic or optical mass storage, short or long term storage media, or any other non-transitory computer-readable medium capable of storing programming instructions for execution by the control module 802. The computer-executable programming instructions, when read and executed by the control module 802, cause the control module 802 to perform the tasks, operations, functions, and processes described in greater detail below. In this regard, the control scheme or algorithm implemented by the control module 802 may be realized as control application code that is stored or otherwise maintained in the memory 806 and executed by the control module 802 to implement or otherwise provide one or more of the closed-loop PID control components in software. For example, the control application code may be executed by the control module 802 to implement or otherwise provide one or more of the components or functional modules of the control system 500 of FIG. 5 and implement the control process 600 of FIG. 6.

As described above with reference to FIGS. 4-7, in exemplary embodiments, the control module 802 obtains a target glucose value for the user associated with the infusion device 702, obtains a sensed glucose value from the glucose sensing arrangement 704, and performs PID control to regulate the measured value to the target value. For example, the control module 802 may include or otherwise implement a summation block that determines a difference between the target glucose value and the sensed glucose value, a proportional gain block that multiplies the difference by a proportional gain coefficient, integration and gain blocks that multiply the integrated difference by an integration gain coefficient, and derivative and gain blocks that multiply the derivative of the difference by a derivative gain coefficient.

In the illustrated embodiment of FIG. 8, the data storage element 808 generally represents the hardware, circuitry and/or other components of the pump control system 720 that are configured to store the closed-loop control information for the control scheme implemented by the control module 802. In this regard, the data storage element 808 may store or otherwise maintain the control parameters for the closed-loop control (e.g., the target glucose value, the proportional gain coefficient, the integration gain coefficient, the derivative gain coefficient, insulin delivery limits, threshold values, and the like). Additionally, the data storage element 808 may store or otherwise maintain the notification parameters for the user's alert configuration information, which defines the manner in which user notifications should be provided while operating the infusion device 702 in accordance with the closed-loop control parameters. In a similar manner as described above in the context of the memory 806, the data storage element 808 may be realized as any sort of RAM, ROM, flash memory, registers, hard disks, removable disks, magnetic or optical mass storage, short or long term storage media, or any other non-transitory computer-readable medium. That said, in exemplary embodiments, the data storage element 808 is realized a plurality of registers associated with the control and notification parameters for the closed-loop, and accordingly, the data storage element 808 may alternatively be referred to herein as the parameter registers.

Figure 9:
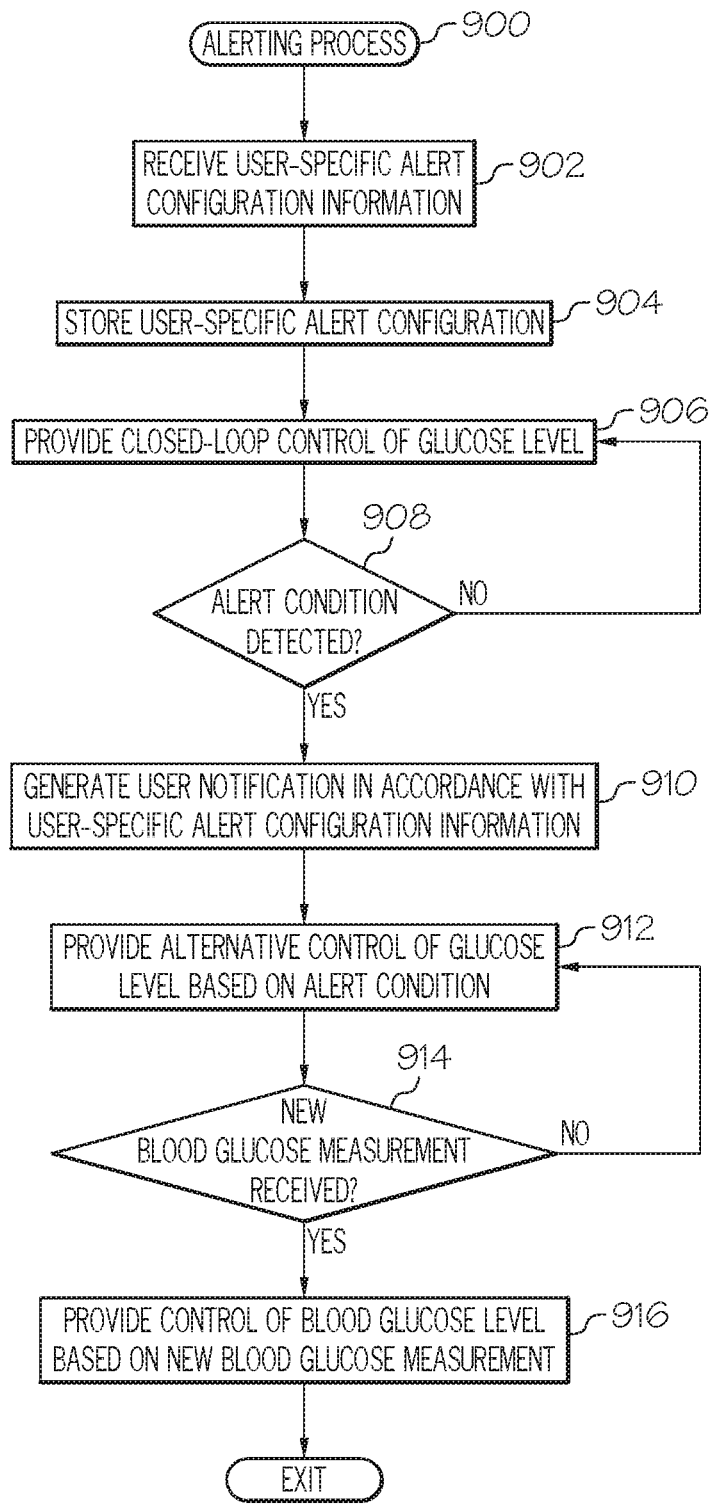
FIG. 9 is a flow diagram of an exemplary alerting process suitable for use with an infusion system.

FIG. 9 depicts an exemplary alerting process 900 suitable for implementation by a control system associated with a fluid infusion device to automatically provide user notifications in a user-specific (or user-configurable) manner while providing closed-loop control of the condition in the body of the user that is influenced by the fluid delivered by the fluid infusion device. The various tasks performed in connection with the alerting process 900 may be performed by hardware, firmware, software executed by processing circuitry, or any combination thereof. For illustrative purposes, the following description refers to elements mentioned above in connection with FIGS. 1-8. In practice, portions of the alerting process 900 may be performed by different elements of an infusion system, such as, for example, the infusion device 702, the glucose sensing arrangement 704, the blood glucose meter 706, the user interface element(s) 708, and/or the pump control system 720 in the infusion system 700 of FIG. 7. It should be appreciated that the alerting process 900 may include any number of additional or alternative tasks, the tasks need not be performed in the illustrated order and/or the tasks may be performed concurrently, and/or the alerting process 900 may be incorporated into a more comprehensive procedure or process having additional functionality not described in detail herein. Moreover, one or more of the tasks shown and described in the context of FIG. 9 could be omitted from a practical embodiment of the alerting process 900 as long as the intended overall functionality remains intact.

In exemplary embodiments, the alerting process 900 initializes or otherwise begins by receiving or otherwise obtaining alert configuration information for a user and storing or otherwise maintaining the user's alert configuration information (tasks 902, 904). In this regard, the user or patient associated with the infusion device 702 or another individual (e.g., a doctor, nurse, caregiver, or the like) may manipulate an input user interface element 708 to interact with the pump control system 720 to configure the alerts or notifications to be generated by the pump control system 720 during closed-loop control of the user's glucose level. In practice, the pump control system 720 may generate or otherwise provide one or more graphical user interface (GUI) displays on a display device associated with the infusion device 702 (which may be a user interface element 708 integrated with the infusion device 702 or part of another device 106, 108 communicatively coupled to the infusion device 102, 702) that include a menu or list of the various different alertable conditions that may be detected by the pump control system 720 during closed-loop control of the user's blood glucose level. For example, as described above in the context of FIGS. 5-6, the pump control system 720 may be configured to detect when the infusion device 702 provides continuous delivery of insulin at a maximum insulin limit for greater than a threshold amount of time, when the infusion device 702 provides delivery of insulin that is less than or equal to a minimum allowable infusion of zero for greater than a threshold amount of time, when an estimated (or model-predicted) glucose differs from the sensor glucose value obtained from the glucose sensing arrangement 704 is greater than a threshold value, when the pump control system 720 and/or the infusion device 702 fails to receive data packets from the glucose sensing arrangement 704, when the closed-loop mode should be exited (e.g., when a closed-loop control time limit has been reached), and the like.

In exemplary embodiments, the GUI display(s) provided by the pump control system 720 include GUI elements (e.g., buttons, checkboxes, or the like) that are selectable by the user to indicate or otherwise identify the conditions that the user would like to receive notifications of, along with GUI elements that are selectable by the user to indicate or otherwise identify the type of notification that the user would like to receive when that respective condition is detected by the pump control system 720. For example, the user may manipulate the GUI elements to indicate that the user would like to receive a visual notification when the missed transmission module 516 and/or the pump control system 720 detects missed data packets from the glucose sensing arrangement 704 for a duration of time that is less than a lower threshold of amount time (e.g., 15 minutes), both a visual and a haptic notification when the missed transmission module 516 and/or the pump control system 720 detects missed data packets from the glucose sensing arrangement 704 for a duration of time that is greater than the lower threshold of amount time but less than an upper threshold amount of time (e.g., 60 minutes), and visual, haptic, and auditory notifications when the missed transmission module 516 and/or the pump control system 720 detects missed data packets from the glucose sensing arrangement 704 for a duration of time that is greater than the upper threshold amount of time. In some embodiments, the GUI display(s) provided by the pump control system 720 may include GUI elements that allow the user to set or otherwise adjust the thresholds used by the pump control system 720 to detect the various alertable conditions. For example, a user may increase or decrease the threshold for a particular condition based on the user's personal preferences with respect to when and/or how frequently the user would like to be notified. Additionally, the user may provide configuration information that defines whether or not a particular user notification should be repeated when a user response is not received (e.g., to ensure that the user has received the notification), and if so, the frequency and/or manner in which the user notification should be repeated.

In embodiments where the pump control system 720 supports remote notifications (e.g., via text message or other short messaging service, e-mail, or the like), the GUI display(s) provided by the pump control system 720 may include GUI elements that allow the user to provide the desired destination address for the remote notification (e.g., the phone number, e-mail address, or the like) that will be provided for the particular detected condition. In this regard, remote notifications may be sent to other individuals in different situations, as desired by the user, so that other individuals may be apprised of the user's physical condition and aid or otherwise assist the user, as needed. After selecting the desired GUI elements to indicate the conditions that the user would like to be alerted of, the types and/or numbers of notifications that the user would like to receive for those selected conditions, and/or any user-configured thresholds for those selected conditions, the user may manipulate another GUI element to confirm or otherwise save his or her alert configuration information.

In exemplary embodiments, after receiving selection or indication of which conditions that the user would like to be notified of along with the types of notifications that the user would like to receive for those respective conditions, the pump control system 720 stores or otherwise maintains that user-specific alert configuration information for reference while providing closed-loop control of the user's blood glucose level. For example, the pump control system 720 may store or otherwise maintain data or information in the parameter registers 808 that corresponds to the selected GUI elements on the GUI display provided by the pump control system 720. Thus, the data or information stored in the parameter registers 808 define the manner in which the user associated with the infusion device 702 would like to be notified during implementation of the closed-loop mode.

Still referring to FIG. 9, the alerting process 900 continues by operating the fluid infusion device to provide closed-loop control of the user's glucose level and detecting or otherwise identifying an alert condition while providing the closed-loop control (tasks 906, 908). As described above in the context of FIGS. 5-6, the pump control system 720 may initiate the control process 600 in response to a user-initiated command, automatically in response to the detection of operating conditions that are usually indicative of closed-loop operation (e.g., that the user is sleeping), or otherwise determining that it is desired to enter the closed-loop operating mode. Once in the closed-loop mode, the pump control system 720 utilizes glucose measurement data (e.g., the current SG value 540, the current sensor Isig value 550, and the like) received from the glucose sensing arrangement 704 to determine a sensor glucose value and applies the PID gain coefficients to the difference between the sensor glucose value and a target glucose value to obtain delivery commands provided to the motor control module 712 for operating the motor 732. While in the closed-loop mode, the pump control system 720 implements or otherwise provides a number of modules 512, 514, 516 that monitor for alertable conditions, as described above.

In response to detecting an alert condition, the alerting process 900 generates or otherwise provides one or more user notifications in accordance with the user's alert configuration information for that particular type of alert condition (task 910). In this regard, when a module 512, 514, 516 of the pump control system 720 detects an alert condition, the pump control system 720 accesses the user's alert configuration information stored in the parameter registers 808 to determine whether the user has selected or otherwise indicated that he or she would like to be notified of that detected condition, along with the manner in which the user would like to be notified. When the pump control system 720 determines the user would like to be notified of the detected condition, the pump control system 720 automatically generates or otherwise provides one or more user notifications in accordance with the user's alert configuration information for that detected condition. For example, if the user's alert configuration information indicates that the user would like to receive an auditory notification when the model supervisor module 514 detects the estimated blood glucose differs from the measured sensor glucose value obtained via the glucose sensing arrangement 704 by more than a threshold value, the pump control system 720 automatically operates a speaker or other audio output interface element 708 associated with the infusion device 702 to provide an auditory notification (or indication) of the deviation between the estimated blood glucose value and the measured sensor glucose value in response to the model supervisor module 514 detecting the deviation. For remote notifications (e.g., text messages, e-mails, or the like), the pump control system 720 may automatically initiate transmission of a remote notification to the destination address(es) stored in the parameter registers 808. In some embodiments, the remote notification may identify, describe, or otherwise detail the alerted condition that was detected by the pump control system 720 to provide guidance to the recipient or otherwise aid the recipient's understanding of the alerted condition.

Still referring to FIG. 9, in accordance with one or more embodiments, the alerting process 900 continues by providing alternative control of the user's glucose level based on the detected alert condition until receiving a response to the generated user notification(s), and thereafter provides control of the user's glucose level in a manner that is influenced by or otherwise based on the received user response (tasks 912, 914, 916). In this regard, as described above in the context of FIGS. 5-6, after a module 512, 514, 516 of the pump control system 720 detects a particular alertable condition, the pump control system 720 may provide alternative control of the glucose level in lieu of the closed-loop control, such as, for example, by generating delivery commands that operate the motor 732 to provide a pre-programmed safe basal rate (e.g., block 582) or a pre-programmed open-loop overnight basal rate (e.g., blocks 976, 984) based on the particular condition detected. In exemplary embodiments, the pump control system 720 automatically generates or otherwise provides user notifications to apprise the user that the closed-loop control mode has been exited and an alternative control mode is being implemented in accordance with the user's alert configuration information. For example, the pump control system 720 may automatically generate a visual notification on a display device that indicates that the closed-loop control mode has been suspended, terminated, or otherwise exited and identifies the alternative control mode that is currently being implemented by the pump control system 720. In some embodiments, the user may also configure the pump control system 720 to automatically generate notifications while implementing the alternative control mode in a similar manner as described herein in the context of the closed-loop control mode.

As described in greater detail below in the context of FIG. 10, in response to receiving a notification, the user may manipulate a user interface element 708 associated with the infusion device 702 and/or the blood glucose meter 706 to provide a response to the pump control system 720 and/or the infusion device 702 in an attempt to resume the closed-loop control mode and/or override the alternate control mode being provided by the pump control system 720. Based on the response received from the user, the pump control system 720 proceeds with operating the infusion device 702 and/or the motor 732 to deliver fluid to the user in a manner that is influenced by the received user response.

For example, when the user operates the blood glucose meter 706 to obtain a new blood glucose measurement value that is provided to the pump control system 720 and/or the infusion device 702 to reinitialize the closed-loop control mode (e.g., when the user notification was generated by the insulin delivery timeout module 512 based on the insulin delivery exceeding and/or failing to meet a delivery limit or by the model supervisor module 514 based on the deviation between the estimated blood glucose value and the measured sensor blood glucose value), the pump control system 720 and/or the infusion device 702 may reinitialize the closed-loop control mode and resume providing closed-loop control based at least in part on the new blood glucose measurement value. In other embodiments, the user may simply manipulate a user interface element 708 to attempt cause the pump control system 720 to reinitialize the closed-loop control mode (e.g., after replacing the glucose sensing arrangement 704 or manipulating the glucose sensing arrangement 704 and/or the infusion device 702 in a manner that is intended to improve transmissions when the user notification is generated by the missed transmission module 516 based on missed transmissions), whereby the pump control system 720 and/or the infusion device 702 may reinitialize the closed-loop control mode and resume providing closed-loop control based on resumed transmissions with the glucose sensing arrangement 704. In yet other embodiments, the user may manipulate a user interface element 708 to cause the pump control system 720 to transition to a manual (or user-controlled) operating mode.

In this manner, the user response allows the pump control system 720 to proceed with providing control of the user's glucose level in a user-specific manner, based on the user's response to the particular user notifications generated by the pump control system 720. For example, some users may choose to simply allow the pump control system 720 to provide open-loop control of the glucose level, while other users may choose to be more proactive with attempts to reinitialize the closed-loop control mode, while other users may choose to simply disable any automatic control of insulin delivery and revert to a manual operating mode. Even among proactive users, some users may attempt to reinitialize the closed-loop control using solely a new blood glucose measurement value from the blood glucose meter 706, while other users may also replace the glucose sensing arrangement 704 (or a battery associated therewith) before attempting to reinitialize the closed-loop control. Thus, not only may each individual user be alerted in his or her own uniquely desired manner in accordance with his or her user-specific alert configuration scheme, but each individual user also can individually determine how to respond to alert notifications, thereby enabling the pump control system 720 to proceed after the notifications in a more personalized or user-configurable manner based on the response received from the user.

Figure 10:
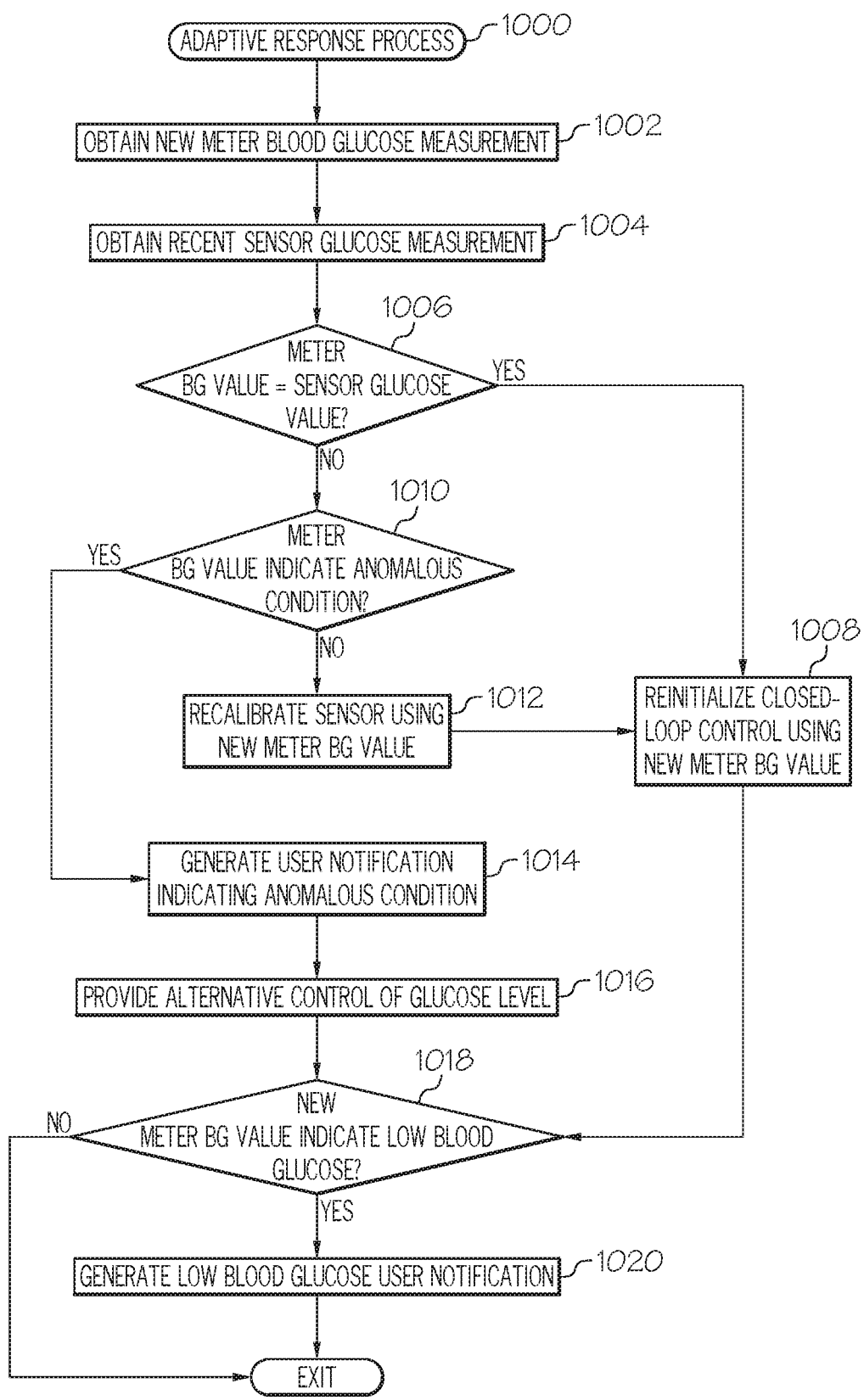
FIG. 10 is a flow diagram of an exemplary adaptive response process suitable for use in conjunction with the alerting process of FIG. 9.

FIG. 10 depicts an exemplary adaptive response process 1000 suitable for implementation in conjunction with the alerting process 900 of FIG. 9 (e.g., task 916) to adjust or otherwise modify the manner in which a fluid infusion device is being controlled based on a response received from a user. The various tasks performed in connection with the adaptive response process 1000 may be performed by hardware, firmware, software executed by processing circuitry, or any combination thereof. For illustrative purposes, the following description refers to elements mentioned above in connection with FIGS. 1-8. In practice, portions of the adaptive response process 1000 may be performed by different elements of an infusion system, such as, for example, the infusion device 702, the glucose sensing arrangement 704, the blood glucose meter 706, the user interface element(s) 708, and/or the pump control system 720 in the infusion system 700 of FIG. 7. It should be appreciated that the adaptive response process 1000 may include any number of additional or alternative tasks, the tasks need not be performed in the illustrated order and/or the tasks may be performed concurrently, and/or the adaptive response process 1000 may be incorporated into a more comprehensive procedure or process having additional functionality not described in detail herein. Moreover, one or more of the tasks shown and described in the context of FIG. 10 could be omitted from a practical embodiment of the adaptive response process 1000 as long as the intended overall functionality remains intact.

In exemplary embodiments, the adaptive response process 1000 begins by receiving or otherwise obtaining an updated (or new) blood glucose measurement for the user from a blood glucose meter (task 1002). In this regard, an updated (or new) measurement for use as the reference meter BG value 520 is obtained using the blood glucose meter 706. For example, in response to a user notification generated by the pump control system 720, the user may manipulate or otherwise operate the blood glucose meter 706 to obtain a new blood glucose measurement value and transmit the new blood glucose measurement value to the pump control system 720 to reinitialize the closed-loop control mode. In exemplary embodiments, the pump control system 720 stores or otherwise maintains the updated blood glucose reference measurement value, for example, by overwriting the existing meter BG value 520 with the updated (or new) blood glucose measurement value.

The adaptive response process 1000 continues by receiving or otherwise obtaining a recent interstitial fluid glucose measurement and determining whether the interstitial fluid glucose measurement matches or otherwise corresponds to the new meter blood glucose measurement value (tasks 1004, 1006). Depending on the embodiment, the pump control system 720 may obtain the most recent sensor glucose value (e.g., from a data storage element 806, 808) or wait until an updated (or new) sensor glucose value is transmitted by the glucose sensing arrangement 704 or is otherwise available. Thereafter, the pump control system 720 compares the most recent sensor glucose value 540 to the updated (or new) meter BG value 520 to determine whether the most recent sensor glucose value 540 is substantially equal to the updated meter BG value 520. In one embodiment, the pump control system 720 determines the most recent sensor glucose value 540 is substantially equal to the updated meter BG value 520 when the most recent sensor glucose value 540 is within thirty percent of the updated meter BG value 520 when the updated meter BG value 520 is greater than 80 mg/dL, or alternatively, when the most recent sensor glucose value 540 is within 15 mg/dL of the updated meter BG value 520 when the updated meter BG value 520 is less than 80 mg/dL.

When the new meter BG value is substantially equal to the most recent sensor glucose value, the adaptive response process 1000 determines that the meter and interstitial glucose measurement values match and allows the closed-loop control mode to be reinitialized using the new meter BG measurement value (task 1008). In this regard, the closed-loop initiation module 502 of the pump control system 720 references or otherwise utilizes the updated meter BG value 520 when determining whether the closed-loop mode can be initiated in conjunction with the control process 600 of FIG. 6.

In one or more exemplary embodiments, after confirming the updated meter BG value 520 and the sensor glucose value 540 match, the pump control system 720 also resets one or more counters, timers, or the like used to identify alert conditions upon reinitialization of the closed-loop mode. For example, the insulin delivery timeout module 512 may reset any timers or counters used to monitor the insulin delivery rate, so that the original limits or thresholds apply for the subsequent instantiation of the closed-loop mode. Thus, if the alert condition that triggered the user notification was detected by the insulin delivery timeout module 512, after confirming that the sensor glucose value 540 is accurate or otherwise matches the updated meter BG value 520, the closed-loop control mode may be allowed to resume continuous delivery of insulin at an insulin delivery limit for the original time limit. For example, the insulin delivery timeout module 512 may detect an alert condition when a maximum insulin delivery rate limit is continuously provided for a three hour time limit, and in response, the pump control system 720 may generate a user notification in accordance with the user's alert configuration information that indicates to the user that the maximum continuous insulin delivery rate limit has been met. In response, after the user manipulates the blood glucose meter 706 to provide an updated meter BG value 520 that confirms the sensor glucose value 540 is accurate, the insulin delivery timeout module 512 is reset or reinitialized so that the subsequent iteration of the closed-loop control mode may also be allowed to continuously provide the maximum insulin delivery rate for three hours before another alert condition is detected. In some embodiments, other limitations on the closed-loop mode are maintained unchanged upon reinitiating the closed-loop mode. For example, if the closed-loop mode is limited in duration to only eight hours in a twenty-four hour window, the counters and/or timers that monitor the duration in which closed-loop mode has been utilized during the course of the preceding twenty-four hours are not reset to prevent the closed-loop mode from being implemented for more than eight hours in a twenty-four hour window.

Still referring to FIG. 10, when the adaptive response process 1000 determines that the new meter BG value does not match the sensor glucose value, the adaptive response process 1000 determines whether the difference between the new meter BG value and the most recent sensor glucose value indicates an anomalous condition of the interstitial glucoses sensing arrangement (task 1010). In one or more embodiments, the pump control system 720 calculates or otherwise determines a sensor calibration factor for the glucose sensing arrangement 704 based on the updated meter BG value 520 and the most recent sensor Isig value 524, and identifies an anomalous condition when that sensor calibration factor is not within an acceptable range of values for the glucose sensing arrangement 704. For example, the pump control system 720 may identify an anomalous condition when the sensor calibration factor is less than 2.5 or greater than 12. In some embodiments, the pump control system 720 may identify an anomalous condition when a difference between the updated meter BG value 520 and the most recent sensor glucose value 540 is greater than a threshold value indicative of an anomalous condition.

When the adaptive response process 1000 determines that an anomalous condition of the interstitial glucose sensing arrangement does not exist, the adaptive response process 1000 proceeds by recalibrating the interstitial glucose sensing arrangement using the new meter BG value (task 1012). In this regard, the pump control system 720 may calculate or otherwise determine an updated (or new) sensor calibration factor 522 for the glucose sensing arrangement 704 based on the relationship between updated meter BG value 520 and the most recent sensor Isig value 524, and update the timestamp data 526 to reflect the updated calibration time. In accordance with one or more embodiments, the pump control system 720 stores or otherwise maintains previous meter BG values 520 and their corresponding sensor Isig values 524 (e.g., the sensor Isig value 524 contemporaneous to a respective meter BG value 520) and calculates the updated sensor calibration factor 522 based on the relationship between updated meter BG value 520 and the most recent sensor Isig value 524 along with the relationship between the previous meter BG values and sensor Isig values. In one embodiment, the pump control system 720 determines the updated sensor calibration factor 522 based on the updated meter BG value 520, the most recent sensor Isig value 524, the three previous meter BG values and their associated sensor Isig values. After recalibrating the interstitial glucose sensing arrangement, the adaptive response process 1000 continues by reinitializing the closed-loop control mode using the new meter BG measurement value with the new sensor calibration factor for the interstitial glucose sensing arrangement (task 1008). In this regard, the closed-loop initiation module 502 of the pump control system 720 may utilize the updated sensor calibration factor 522 and the updated calibration time 526 along with the updated meter BG value 520 when determining whether the closed-loop mode can be initiated in conjunction with the control process 600 of FIG. 6.

In the illustrated embodiment of FIG. 10, when the adaptive response process 1000 identifies an anomalous condition, the adaptive response process 1000 continues by generating or otherwise providing a user notification indicating the anomalous condition (task 1014). For example, the pump control system 720 may generate or otherwise provide a visual or graphical user notification on the infusion device 702, the glucose sensing arrangement 704, or via another remote device communicatively coupled to the pump control system 720 (e.g., the CCD 106, the computer 108, or the like) that notifies the user that the glucose sensing arrangement 704 should be repaired, replaced, or otherwise modified before the closed-loop control mode can be reinitiated. In exemplary embodiments, the pump control system 720 generates the user notification in accordance with the user's alert configuration information in a similar manner as described above. For example, when the user normally uses the closed-loop control mode overnight while sleeping, the user may desire that a text message, e-mail message, or another remote notification be generated that the user can receive the next day via the user's mobile device, personal computer, or the like (e.g., the CCD 106, the computer 108, or the like) to remind the user to remedy or otherwise address the anomalous condition of the glucose sensing arrangement 704.

In exemplary embodiments, when the adaptive response process 1000 identifies an anomalous condition, the adaptive response process 1000 provides an alternative control of the user's glucose level in lieu of reinitializing the closed-loop mode (task 1016). In this regard, the pump control system 720 may operate the motor 732 in accordance with the alternative control mode identified based on the type of alert condition that was previously detected by the pump control system 720. For example, as described above in the context of FIG. 5, if the alert condition was detected by the model supervisor module 514 based on a deviation between the estimated glucose value and the sensor glucose value and the updated meter BG value 520 indicates an anomalous condition of the interstitial glucose sensing arrangement 704, the pump control system 720 may operate the motor 732 in an open-loop mode to provide an overnight basal delivery rate to the user (e.g., block 976). Conversely, if the updated meter BG value 520 does not indicate an anomalous condition of the interstitial glucose sensing arrangement 704, the pump control system 720 operates the motor 732 in the closed-loop mode (e.g., block 574) using the updated (or new) sensor calibration factor 522 (e.g., tasks 1008, 1012).

Still referring to FIG. 10, in exemplary embodiments, the adaptive response process 1000 also identifies or otherwise determines whether the new meter blood glucose measurement value is indicative of a potential low blood glucose condition, and if so, generates or otherwise provides a user notification that indicates the potential low blood glucose condition (e.g., tasks 1018, 1020). In this manner, the pump control system 720 automatically notifies the user of the potential low blood glucose condition so that the user may take appropriate corrective action. For example, the pump control system 720 may generate or otherwise provide a visual and/or auditory notification that indicates that the user should consume carbohydrates to raise his or her blood glucose level. Again, the low blood glucose user notification may be generated in accordance with the user's alert configuration information, so that the user may control the manner in which he or she is notified. For example, some users may be content with only a visual low blood glucose notification, while other users may desire an additional auditory and/or a haptic notification of the potential low blood glucose condition.

For the sake of brevity, conventional techniques related to glucose sensing and/or monitoring, sensor calibration and/or compensation, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion system comprising:
one or more user interface elements;
a motor operable to deliver fluid to a user, delivery of the fluid influencing a condition of the user;
a sensing arrangement to obtain a sensor value indicative of the condition of the user;
a data storage element to store alert configuration information for the user; and
a control system coupled to the motor, the sensing arrangement, the data storage element, and the one or more user interface elements to:
operate the motor to deliver the fluid to the user based at least in part on the sensor value;
identify an alert condition based at least in part on the alert configuration information for the user while operating the motor; and
in response to identifying the alert condition, provide a user notification via the one or more user interface elements in accordance with the alert configuration information.

2. The infusion system of claim 1, wherein the control system detects the alert condition based at least in part on the sensor value.

3. The infusion system of claim 2, wherein the control system operates the motor in a closed-loop mode to deliver the fluid to the user based at least in part on a difference between a target value for the condition of the user and the sensor value and detects the alert condition based at least in part on the sensor value while operating the motor in the closed-loop mode.

4. The infusion system of claim 1, wherein:
the alert configuration information includes one or more user-specific thresholds; and
the control system determines a type or a number for the user notification based on the one or more user-specific thresholds.

5. The infusion system of claim 1, wherein:
the alert configuration information identifies a type of user notification to be generated for the alert condition; and
the control system automatically generates the type of user notification identified by the alert configuration information for the user in response to identifying the alert condition.

6. The infusion system of claim 1, wherein:
the alert configuration information identifies a number of user notifications to be generated for the alert condition; and
the control system automatically generates the number of user notifications identified by the alert configuration information for the user in response to identifying the alert condition.

7. The infusion system of claim 1, wherein the alert configuration information defines a frequency for repeating the user notification.

8. The infusion system of claim 1, wherein the control system determines content of the user notification based on the alert configuration information.

9. The infusion system of claim 1, the user notification comprising a remote user notification, wherein the control system determines one or more destination addresses for the remote user notification based on the alert configuration information.

10. The infusion system of claim 1, wherein the alert configuration information indicates conditions selectable by the user for which the user would like to receive notifications.

11. The infusion system of claim 1, wherein the one or more user interface elements comprise an output user interface of an infusion device indicated by the alert configuration information for the alert condition.

12. The infusion system of claim 1, wherein the control system provides a second user notification in accordance with the alert configuration information in response to receiving a user response from the user after providing the user notification.

13. The infusion system of claim 12, further comprising a blood glucose meter, wherein:
the user response comprises an updated blood glucose measurement value from the blood glucose meter; and
the second user notification comprises a low blood glucose user notification or an anomalous sensor notification automatically generated by the control system based at least in part on the updated blood glucose measurement value.

14. An infusion system comprising:
one or more user interface elements;
a motor operable to deliver fluid to a user, delivery of the fluid influencing a condition of the user;
a sensing arrangement to obtain a sensor value indicative of the condition of the user;
a data storage element to store alert configuration information for the user; and
a control system coupled to the motor, the sensing arrangement, the data storage element, and the one or more user interface elements to:
operate the motor in a closed-loop mode to deliver the fluid to the user based at least in part on a difference between a target value for the condition of the user and the sensor value;
identify an alert condition based at least in part on the alert configuration information for the user while operating the motor in the closed-loop mode; and
in response to identifying the alert condition, provide a user notification via the one or more user interface elements in accordance with the alert configuration information.

15. The infusion system of claim 14, further comprising a blood glucose meter to obtain a blood glucose reference measurement value from a body of the user, wherein:
the control system is coupled to the blood glucose meter and the sensing arrangement to:
operate the motor in the closed-loop mode based at least in part on an initial blood glucose reference measurement value from the blood glucose meter; and
after providing the user notification:
receive an updated blood glucose reference measurement value for the user from the blood glucose meter; and
provide a second user notification based at least in part on the updated blood glucose reference measurement value via the one or more user interface elements in accordance with the alert configuration information.

16. The infusion system of claim 14, wherein:
the one or more user interface elements comprise:
a first user interface element associated with a first type of user notification; and
a second user interface element associated with a second type of user notification; and
the control system is coupled to the first user interface element and the second user interface element to:

provide the user notification via the first user interface element when the alert configuration information identifies the first type of user notification for the alert condition; and provide the user notification via the second user interface element when the alert configuration information identifies the second type of user notification for the alert condition.

17. The infusion system of claim 14, wherein the control system receives the alert configuration information from the user via the one or more user interface elements and stores the received alert configuration information in the data storage element.

18. The infusion system of claim 14, wherein:
the alert configuration information identifies a type of user notification to be generated for the alert condition; and
the user notification is provided via an output user interface of the one or more user interface elements corresponding to the type of user notification.

19. The infusion system of claim 14, wherein:
the alert configuration information includes one or more user-specific thresholds; and
the user notification is generated based on the one or more user-specific thresholds.

20. An infusion device comprising:
one or more input user interface elements to receive alert configuration information for a user;
one or more output user interface elements;
a motor operable to deliver fluid to the user, delivery of the fluid influencing a condition of the user;
a data storage element to store the alert configuration information; and
a control system coupled to the motor, the data storage element, the one or more input user interface elements, and the one or more output user interface elements to:
operate the motor to deliver the fluid to the user based at least in part on a target value for the condition;
identify an alert condition based at least in part on the alert configuration information for the user while operating the motor; and
in response to identifying the alert condition, provide a user notification via the one or more output user interface elements in accordance with the alert configuration information.

* * * * *